(12) United States Patent
Michikawa et al.

(10) Patent No.: US 6,462,190 B1
(45) Date of Patent: Oct. 8, 2002

(54) POLYNUCLEOTIDES AND KITS FOR DETECTION OF AN AGE-RELATED MUTATION

(75) Inventors: Yuichi Michikawa, South Pasadena; Giuseppe M. Attardi, Altadena, both of CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/549,804

(22) Filed: Apr. 14, 2000

Related U.S. Application Data

(60) Provisional application No. 60/129,326, filed on Apr. 14, 1999.

(51) Int. Cl.[7] .................. C07H 21/04; C12P 21/06; C12N 1/21; C12N 5/10; C12N 15/63
(52) U.S. Cl. .................. 536/24.1; 536/23.1; 536/24.31; 435/69.1; 435/252.3; 435/320.1; 435/325
(58) Field of Search .................. 536/23.1, 24.1, 536/24.31; 435/69.1, 252.3, 320.1, 325, 810

(56) References Cited

U.S. PATENT DOCUMENTS 6,027,883 A    2/2000    Hernstadt et al. ............. 435/6

FOREIGN PATENT DOCUMENTS

WO    WO 98/23632    6/1998

OTHER PUBLICATIONS

Anderson et al., "Sequence and organization of the human mitochondrial genome," *Nature*, 290:457–465 (Apr. 9, 1981).

Fleming et al., "Age Dependent Changes in Mitochondria," *Symposium on Molecular Biology of Aging* (1984:Brookhaven National Laboratory), pp. 143–156.

Fleming et al., "Is Cell Aging Caused by Respiration–Dependent Injury to the Mitochondrial Genome?" *Gerontology*, 28:44–53 (1982).

Jazin et al., "Human brain contains high levels of heteroplasmy in the noncoding regions of mitochondrial DNA," *Proc. Natl. Acad. Sci. USA*, 93:12382–12387 (Oct. 1996).

Larsson et al., "Progressive Increase of the Mutated Mitochondrial DNA Fraction in Kearns–Sayre Syndrome," *Pediatric Research*, 28(2):131–136 (1990).

Linnane et al., "Mitochondrial DNA Mutations as an Important Contributor to Ageing and Degenerative Diseases," *The Lancet*, pp. 642–645 (Mar. 25, 1989).*

Linnane et al., "Mitochondrial Gene Mutation: The Ageing Process and Degenerative Diseases," *Biochemistry International*, 22(6):1067–1076 (Dec. 1990).*

(List continued on next page.)

*Primary Examiner*—Carla J. Myers
*Assistant Examiner*—Diana Johannsen
(74) *Attorney, Agent, or Firm*—Gray Cary Ware & Freidenrich LLP; Lisa A. Haile

(57) ABSTRACT

Provided are polynucleotide sequences useful in detecting age related mutations in a subject as well as methods to identify mutations in mitochondrial sequences.

12 Claims, 31 Drawing Sheets

| DLP6 | Cambridge Number of clones | 285 | 288 | 303 | 315 | 317 | 318 | 321 | 324 | 326 | 327 | 328 | 342 | 356 | 369 | 371 | 372 | 377 | 379 | 389 | 404 | 414 | 428 |
|---|---|---|---|---|---|---|---|---|---|---|---|---|---|---|---|---|---|---|---|---|---|---|---|
| | | C | A | C7T | C5 | C | T | T | C | A | C | A | T | G | C | C | T | C | A | G | C | T | A |
| 20wf | 1 | . | . | C7T | C6 | . | . | . | . | . | . | . | . | . | . | . | . | . | . | . | . | . | . |
|      | 44 | . | . | C8T | C6 | . | . | . | . | . | . | . | . | . | . | . | . | . | . | . | . | . | . |
| 1    | 41 | . | . | C7T | C6 | . | . | . | . | . | . | . | . | . | . | . | . | . | . | . | . | . | . |
|      | 1  | . | . | C7T | C6 | . | . | . | . | . | . | . | . | . | . | . | . | . | . | . | . | . | . |
|      | 1  | . | . | C8T | C6 | . | . | . | . | . | . | . | . | . | . | . | . | . | . | . | . | . | . |
|      | 1  | . | . | C9T | C6 | . | . | . | . | . | . | . | . | . | . | . | . | . | . | . | . | . | . |
| 10   | 1  | . | . | C7T | C6 | . | . | . | . | . | . | . | . | . | . | . | . | . | . | . | . | . | . |
|      | 39 | . | . | C8T | C6 | . | . | . | . | . | . | . | . | . | . | . | . | . | . | . | . | . | . |
|      | 1  | . | . | C8T | C6 | . | . | . | . | . | . | . | . | . | . | . | T | . | . | . | . | . | . |
|      | 2  | . | . | C9T | C6 | . | . | . | . | . | . | . | . | . | . | . | . | . | . | . | . | . | . |
| 13   | 3  | . | . | C8T | C6 | . | . | . | . | . | . | . | . | . | . | . | . | . | . | . | . | . | . |
|      | 27 | . | . | C8T | C6 | . | . | . | . | . | . | . | . | . | . | . | . | . | . | . | . | . | . |
|      | 1  | . | . | C8T | C6 | . | . | . | . | . | . | . | . | . | A | . | . | . | . | . | . | . | . |
|      | 1  | . | . | C8T | C6 | . | . | . | . | . | . | . | . | . | . | – | . | . | . | . | . | . | . |
|      | 1  | . | . | C9T | C6 | . | . | . | . | . | . | . | . | A | . | . | . | . | . | A | . | . | . |

OTHER PUBLICATIONS

T. Ozzawa, "Mitochondrial Genome Mutation in Cell Death and Aging, " *Journal of Bioenergetics and Biomembranes*, 31(4):377–390 (1999).*

Park and Ames, "7–Methylguanine adducts in DNA are normally present at high levels and increase on aging: Analysis by HPLC with electrochemical detection," *Proc. Natl. Acad. Sci. USA*, 85:7467–7470 (Oct. 1988).*

P. Pedersen, "Mitochondrial Events in the Life and Death of Animal Cells: A Brief Overview," *Journal of Bioenergetics and Biomembranes*, 31(4):291–304 (1999).*

Piko et al., "Studies of Sequence Heterogeneity of Mitochondrial DNA from Rat and Mouse Tissues: Evidence for an Increased Frequency of Deletions/Additions with Aging," *Mechanisms of Ageing and Development*, 43:279–293 (1988).*

Richter et al., "Normal oxidative damage to mitochondrial and nuclear DNA is extensive," *Proc. Natl. Acad. Sci. USA*, 85:6465–6467 (Sep. 1988).*

Shigenaga et al., "Oxidative damage and mitochondrial decay in aging, " *Proc. Natl. Acad. Sci. USA*, 91:10771–10778 (Nov. 1994).*

Yoneda et al., "Complementation of Mutant and Wild–Type Human Mitochondrial DNAs Coexisting since the Mutation Event and Lack of Complementation of DNAs Introduced Seperately into a Cell within Distinct Organelles," *Molecular and Cellular Biology*, 14(4):2699–2712 (Apr. 1994).*

Michikawa, Y. et al., "Aging–dependent large accumulation of point mutations in the human mtDNA control region for replication", *Science,* vol. 286, Oct. 22, 1999, pp. 774–779.

Stoneking, M., et al.; "Population variation of human mt DNA control region sequences detected by enzymatic amplification and sequence–specific oligonucleotide probes", *American Journal of Human Genetics,* university of Chicago Press, Chicago, US, vol. 48, No. 2, Feb. 1, 1991, pp. 370–382.

Wallace, D.C., "Mitochondrial genetics: A paradigm for aging and degeneraive diseases?"*Science,* American Association for the Advancement of Science, US, vol. 256, May 1, 1992, pp. 628–632.

* cited by examiner

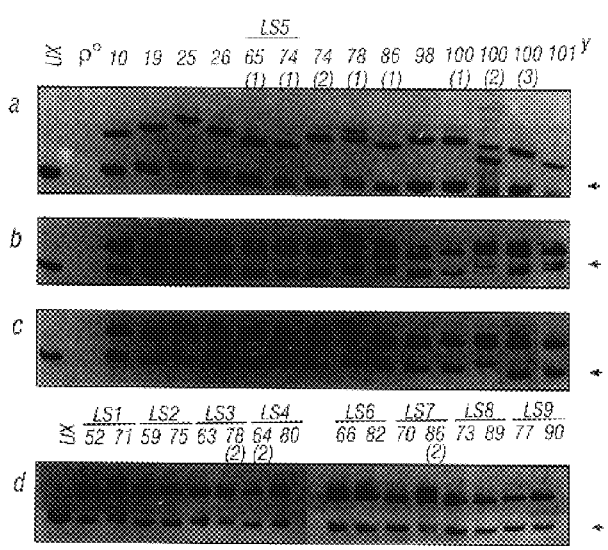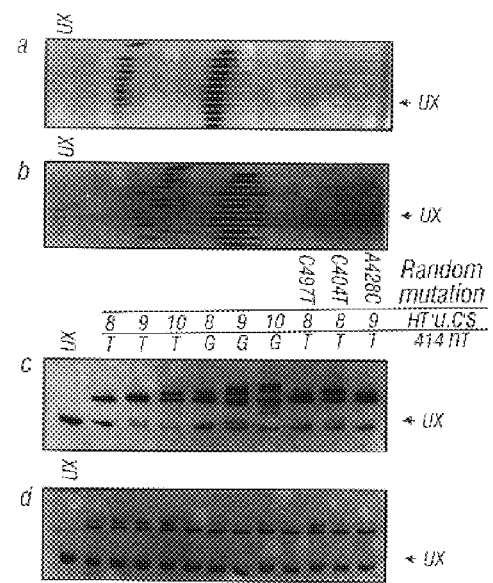
FIG. 2A
FIG. 2B

| Age (y) | DGGE (%) | Primer Extension (%) |
|---|---|---|
| 20wf | 0 | 0 |
| 1 | 0 | 0 |
| 10 | 0 | 0 |
| 13 | 0 | 0 |
| 19 | 0 | 0 |
| 24 | 0 | 0 |
| 25 | 0 | 0 |
| 26 | 0 | 0 |
| 42 | 0 | 0 |
| 48 | 0 | 0 |
| LS1-52 | 0 | 0 |
| LS3-63 | 0 | 0 |
| LS4-64 | 0 | 0 |
| LS6-66 | 35.1 | 23.1 |
| LS7-70 | 3.4 | 1.4 |
| LS1-71 | 0 | 0 |
| LS8-73 | 0 | 0 |
| 78 (1) | 24.4 | 20.8 |
| LS3-78 (2) | 0 | 0 |
| LS4-80 | 50.0 | 31.7 |
| LS6-82 | 12.2 | 3.2 |
| 86 (1) | 42.2 | 27.4 |
| LS7-86 (2) | 23.3 | 24.3 |
| LS8-89 | 0 | 0 |
| 98 | 18.8 | 10.0 |
| 100 (1) | 0 | 4.5 |
| 100 (2) | 0 | 0 |
| 100 (3) | 20.8 | 20.4 |
| 101 | 4.5 | 0 |

FIG. 4D

| FIG. 5A | FIG. 5B | FIG. 5C | FIG. 5D |
|---------|---------|---------|---------|
| FIG. 5E | FIG. 5F | FIG. 5G | FIG. 5H |
| FIG. 5I | FIG. 5J | FIG. 5K | FIG. 5L |
| FIG. 5M | FIG. 5N | FIG. 5O | FIG. 5P |
| FIG. 5Q | FIG. 5R | FIG. 5S | FIG. 5T |
|         |         | FIG. 5U |         |

| DLP6 Cambridge | Number of clones | 285 C | 288 A | 303 — 315 C7TC5 | 317 C | 318 C | 321 T | 324 T | 326 A | 327 A | 328 C | 342 A | 356 T | 369 G | 371 C | 372 T | 377 C | 379 A | 389 G | 404 C | 414 T | 428 A |
|---|---|---|---|---|---|---|---|---|---|---|---|---|---|---|---|---|---|---|---|---|---|---|
| 20wf | 1 | . | . | C7TC6 | . | . | . | . | . | . | . | . | . | . | . | . | . | . | . | . | . | . |
|  | 44 | . | . | C8TC6 | . | . | . | . | . | . | . | . | . | . | . | . | . | . | . | . | . | . |
| 1 | 41 | . | . | C7TC6 | . | . | . | . | . | . | . | . | . | . | . | . | . | . | . | . | . | . |
|  | 1 | . | . | C7TC6 | . | . | . | . | . | . | . | . | . | . | . | . | T | . | . | . | . | . |
|  | 1 | . | . | C8TC6 | . | . | . | . | . | . | . | . | . | A | . | . | . | . | . | . | . | . |
|  | 1 | . | . | C9TC6 | . | . | . | . | . | . | . | . | . | . | – | . | . | . | . | . | . | . |
|  | 1 | . | . | C7TC6 | . | . | . | . | . | . | . | . | A | . | . | . | . | . | . | . | . | . |
| 10 | 39 | . | . | C8TC6 | . | . | . | . | . | . | . | . | . | . | . | . | . | . | . | . | . | . |
|  | 1 | . | . | C8TC6 | . | . | . | . | . | . | . | . | . | . | . | . | . | . | A | . | . | . |
|  | 2 | . | . | C9TC6 | . | . | . | . | . | . | . | . | . | . | . | . | . | . | . | . | . | . |
|  | 3 | . | . | C8TC6 | . | . | . | . | . | . | . | . | . | . | . | . | . | . | . | . | . | . |
| 13 | 27 | . | . | C8TC6 | . | . | . | . | . | . | . | . | . | . | . | . | . | . | . | . | . | . |
|  | 1 | . | . | C8TC6 | . | . | . | . | . | . | . | . | . | . | . | . | . | A | . | . | . | . |
|  | 1 | . | . | C8TC6 | . | . | . | . | . | . | . | . | . | . | . | . | . | . | . | . | . | . |
|  | 1 | . | . | C9TC6 | . | . | . | . | . | . | . | . | . | . | . | . | . | . | . | . | . | . |

```
                                         (CA)6
                                      TA(CA)6  CGCA
    (CA)6                              (CA)5
    (CA)7                              (CA)6
    (CA)7                              (CA)6
    (CA)7                              (CA)7
    (CA)7                              (CA)6
    (CA)7                              (CA)6
    (CA)6
    (CA)7

| | 146 | 150 | 152 | 195 | 227 | 249 | Number of clones |
|---|---|---|---|---|---|---|---|
| | T | C | T | T | A | A | |
| DLP4 | . | . | . | C | . | . | 37 |
| | . | . | C | C | . | G | 11 |
| 48 | . | . | . | . | . | . | 25 |
| 78(1) | . | T | . | . | . | . | 21 |
| | . | T | . | . | G | . | 1 |
| Plasmid[b] | . | . | . | . | . | . | 47 |
| 100(1) | . | . | . | . | . | G | 1 |
| 100(2) | C | . | . | . | . | . | 48 |
| | . | . | C | C | . | . | 33 |
| Cambridge | . | . | . | . | . | . | 15 |

```
  1 gatcacaggt ctatcaccct attaaccact cacgggagct ctccatgcat ttggtatttt
 61 cgtctggggg gtatgcacgc gatagcattg cgagacgctg gagccggagc accctatgtc
121 gcagtatctg tctttgattc ctgcctcatc ctattattta tcgcacctac gttcaatatt
181 acaggcgaac atacttacta aagtgtgtta attaattaat gcttgtagga cataataata
241 acaattgaat gtctgcacag ccactttcca cacagacatc ataacaaaaa atttccacca
301 aaccccccct ccccgcttc tggccacagc acttaaacac atctctgcca aaccccaaaa
361 acaaagaacc ctaaccag cctaaccaga tttcaaattt tatcttttgg cggtatgcac
421 ttttaacagt cacccccca ctaacacatt attttcccct cccactccca tactactaat
481 ctcatcaata caaccccgc ccatcctacc cagcacacac acaccgctgc taacccata
541 cccgaacca accaaaccc aaagacaccc cccacagttt atgtagctta cctccctcaaa
601 gcaatacact gaaatgtttt agacgggctc acatcacccc ataaacaaat aggtttggtc (SEQ ID NO:1)
```

*FIG. 6*

POLYNUCLEOTIDES AND KITS FOR DETECTION OF AN AGE-RELATED MUTATION

CROSS-REFERENCE TO RELATED APPLICATIONS

This application claims priority under 35 U.S.C. § 119(e) to of U.S. Provisional Application No. 60/129,326, filed Apr. 14, 1999, the content of which is herein incorporated by reference in its entirety.

STATEMENT AS TO FEDERALLY-SPONSORED RESEARCH

The U.S. Government has certain rights in this invention pursuant to Grant No. AG12117 awarded by the National Institute of Health.

FIELD OF THE INVENTION

This invention relates to newly identified mitochondrial polynucleotide sequences having age-dependent mutations, and the use of such polynucleotides, as well as the production and isolation of such polynucleotides. More particularly, methods and compositions useful in modulating and diagnosing age-related disorders are provided.

BACKGROUND

Mitochondria are organelles primarily responsible for synthesizing ATP (adenosine triphosphate), the chief store of chemical energy for eukaryotic cells. Oxidative phosphorylation is the process by which ATP is synthesized from ADP with the concomitant oxidation of a reduced substrate derived from the breakdown of sugars and fatty acids. The energy for ATP synthesis is provided by the flow of electrons from the reduced substrate along an electron transport system consisting of a series of electron carriers embedded in the inner mitochondrial membrane. The electron transport system catalyzes the transfer of electrons from reduced substrates to molecular oxygen, resulting in substrate oxidation and reduction of oxygen to water.

Mitochondria generate high levels of reactive oxygen species as by-products of the electron transport process and constitute the main source of free radical generation in eukaryotic cells. Free radicals are believed to act as DNA damaging agents and may be responsible for the high mutation rate of mitochondrial DNA (mtDNA). The metabolic importance of mitochondrial genome-encoded protein products is indicative of the significance of mtDNA-associated mutational events. Such events may be pathogenically involved in degenerative processes, Thus, there is a desire to isolate and identify mutated nucleic acid sequences associated with a mitochondrial dysfunction as it relates to the aging process.

SUMMARY OF THE INVENTION

The invention relates to the identification and quantification of genetic mutations in a mitochondrial control region that segregate with age-related disorders or are age dependent. The invention provides methods for detecting and quantifying such mutations as a diagnostic for an age related disorder, either before or after the onset of clinical symptoms. More specifically, the present invention provides a method for detecting the presence or risk of age-related disorders by obtaining a biological sample containing mitochondrial nucleic acid from a subject and determining the presence of at least one mutation in a mitochondrial DNA main control region including positions 1 and 660 of the Cambridge sequence (Anderson et al., Nature 250:57, 1981), which correlates with the age of a subject. The invention also involves isolated nucleic acid sequences that are useful in the above-mentioned diagnostics, namely those that correspond, or are complementary, to portions of the mitochondrial control region, and where the sequences contain mutations which correlate with age-related disorders.

The invention provides a method for determining the presence or risk of mitochondrial-associated disease or age dependent mutations in a subject by cleaving nucleic acids in a sample containing mitochondrial nucleic acids with one or more enzymes specific for nuclear nucleic acids in order to eliminate nuclear pseudogenes; amplifying a region of interest by contacting the sample with a pair of primers flanking the region of interest; an subjecting one or more amplified products to an analysis to determine a difference in the amplified product sequence compared to a control sequence, wherein a difference is indicative of a mitochondrial-associated disorder or age dependent mutation. In one embodiment, the method of analysis is by denaturing gradient gel electrophoresis (DGGE). In another embodiment the method of amplification and DGGE is repeated one or more times.

The invention also provides an isolated polynucleotide having a sequence as set forth in SEQ ID NO:1 and having one or more of the following mutations selected from the group consisting of T414G, A368G, a T insertion after position 383, T285C, A249G, T195C, T152C, T146C, variations in length or compositon of the homopolymer tract (HT) D310 at positions 303–315 or variations in length or composition of a CA repeat (positions 514–523), and any combination thereof.

The invention further provides a vector containing a polynucleotide sequence of the invention as well as host cells containing the vector.

The invention also provides a method for detecting an age-related disorder, comprising detecting a mutation in a control region of a mitochondrial polynucleotide sequence, wherein the wild type control region has a sequence as set forth in SEQ ID NO:1.

The invention provides a method for diagnosing a subject having or at risk of having an age-related disorder or mutation by determining the presence of at least one mutation in the nucleic acid sequence of a mitochondrial control region wherein the presence of at least one mutation correlates with risk of having an age-related disorder or mutation.

The invention also provides a method for detecting an age-related mutation of DNA by contacting a sample containing mitochondrial DNA with a nucleic acid probe under conditions that allow the probe and the mitochondrial DNA to hybridize; and detecting hybridization of the probe with the DNA, wherein hybridization of the probe to the DNA is indicative of an age-related mutation.

Also provided a kit useful for the detection of an age-related mutations of mitochondrial DNA comprising carrier means containing therein one or more containers wherein a first container contains a nucleic acid probe that hybridizes to a nucleic acid sequence as set forth in SEQ ID NO:1 wherein SEQ ID NO:1 has one or more of the mutations selected from the group consisting of T414G, A368G, a T insertion after position 383, T285C, A249G, T195C, T152C, T146C, variations in length or compositon of the homopolymer tract (HT) D310 at positions 303–315 or variations in length or composition of a CA repeat (positions 514–523), and combinations thereof The invention further provides a method for determining the presence or risk of mitochondrial-associated disease or age dependent mutations in a subject by cleaving nucleic acids in a sample containing mitochondrial nucleic acids with one or more enzymes specific for nuclear nucleic acids in order to eliminate nuclear psudogenes; amplifying a region of interest by contacting the sample with a pair of primers flanking the region of interest; and subjecting one or more amplified products to an analysis to determine a difference in the amplified product sequence compared to a control sequence, wherein a difference is indicative of an mitochondrial-associated disorder or age dependent mutation.

DESCRIPTION OF THE DRAWINGS

These and other aspects will now be described in detail with respect to the accompanying drawings, wherein:

FIG. 6 shows a sequence corresponding to DLP3 to DLP6.

DETAILED DESCRIPTION OF THE INVENTION

Figure 1A:
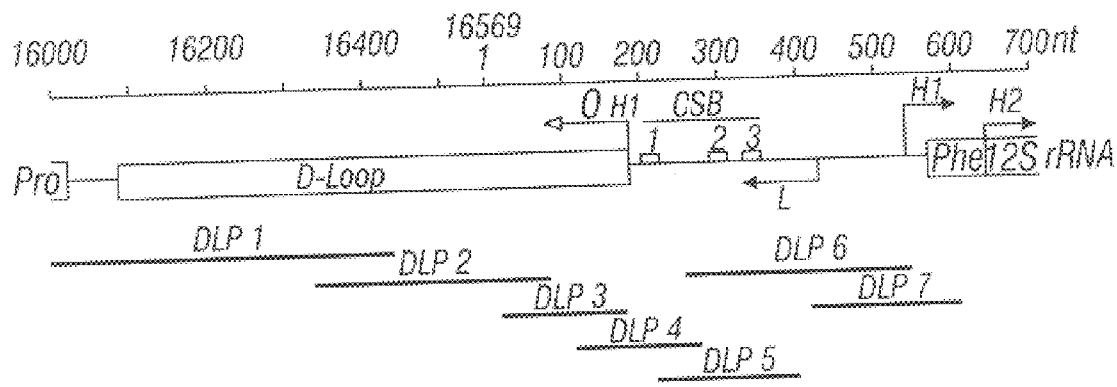
FIG. 1(A) shows map positions of segments into which the main control region of human mtDNA was subdivided for denaturant gradient gel electrophoresis (DGGE) analysis. OH1: primary origin of heavy (H)-strand synthesis. H1, H2, L: start sites for transcription of rDNA, whole H-strand and light (L)-strand and light (L)-strand, respectively. CSB1, CSB2 and CSB3, conserved sequence blocks 1, 2 and 3. Pro, Phe: tRNA$^{Pro}$ and tRNA$^{Phe}$ genes. (B) Shows the effect of different purification steps of mtDNA on PCR amplification with mtDNA- and nuclear DNA digested with BglII, DraIII, RNase A and Exonuclease III. c) Untreated DNA extracted from MN-treated mitochondrial fraction of zhoO 206 cells. d) Same DNA as in c), after digestion with BglII, DraIII and Exonuclease III. e) DNA extracted from micrococcal nuclease (MN)-treated mitochondrial fraction of fibroblasts from 19 year-old individual, and digested as in d). The PCR products were run in a 1.5% agarose gel. ATP: α-subunit of ATP synthase. (C) Shows the effects of different enzymatic treatments on total zhoO 206 cell DNA. R.E.: BglII+DraIII restriction enzymes; ExoIII: Exonuclease III. M: HindIII-digested λ DNA marker. The variously treated DNA samples were run in a 0.6%, agarose gel. (D) shows the scheme of second-DGGE analysis of cloned mtDNA fragments. Shown are the patterns of homoduplexes and/or heteroduplexes expected after hybridization of the PCR products of plasmid DNAs with a randomly chosen cloned fragment

By isolating mutant sequences correlating with age or involved in age-related disorder as described above and elucidating the role of such a mutation in mitochondrial metabolism, it will become possible to use the detection and modification of such a mutant sequence in the diagnosis or treatment of mitochondrial-related diseases as well as in the prevention of aging and the like.

Mitochondria, mtDNA, and Related Pathologies

Most of the mtDNA present in an individual is derived from the mtDNA contained within the ovum at the time of conception. Mutations in mtDNA sequence which affect all copies of mtDNA in a cell are known as homoplasmic. Mutations which affect only some copies of mtDNA are known as heteroplasmic and can vary between different mitochondria in the same cell or same individual.

Each cell in an individual can contain hundreds of mitochondria and each mitochondrion can contain multiple copies of a mitochondrial genome. Cells can harbor mixtures of mutant and normal mtDNA (heteroplasmy). During germline division (meiosis), mutant and normal mitochondria are randomly segregated into daughter cells. Random segregation of mitochondria during meiosis assures that the proportion of mutant to normal mitochondria within a daughter cell will vary. Because the severity of mitochondrial disease is a product of the nature of the mtDNA mutation, i.e., not all mutations will have a similar impact on function, and the proportion of mutant mitochondria in a cell, random segregation of mtDNA causes mitochondrial diseases to appear sporadically in families with variable phenotypes. Offspring derived from an oocyte containing a predominance of normal mitochondria will not express the disease whereas offspring derived from an oocyte containing a predominance of mutant mitochondria will be severely affected. Gradations between these two extremes are also observed.

The D-loop is a stable intermediate formed during the replication of double-stranded mitochondrial DNA genomes. For example, mammalian mitochondrial DNA replication starts at a specific origin of replication, but only one of the two DNA strands of the mitochondria, the so-called H-strand, is synthesized first. In mammalian mitochondria this new synthesis ceases after around 500–700 bases of the H-strand have been synthesized, but the newly synthesized strand is sufficient to displace the original parental strand as a displacement or D-loop. Subsequent DNA replication results in the unidirectional extension of the newly synthesized strand, thereby expanding the D-loop.

The human mitochondrial genome and its products have been suspected of involvement in a number of multisystem degenerative diseases, principally affecting the musculature and nervous system. These suspicions were originally based on: (1) the observation of ultrastructural and biochemical abnormalities of mitochondria in association with several such pathologies; (2) the predominance of maternal inheritance, and (3) the fact that the most commonly affected tissues are those known or believed to be most dependent on respiratory metabolism.

Analysis of mitochondrial DNA (mtDNA) in affected individuals and their families (by for example, restriction enzyme analysis and DNA sequencing) has provided convincing evidence that mutations in mtDNA are involved in these diseases. In most cases a mutant genome is present alongside an ostensibly wild-type genome in the affected individuals (i.e. they are heteroplasmic), and the representation of the mutant genome is sometimes, but not always, correlated with the severity of the condition and with the tissue specificity of symptoms.

Large heteroplasmic deletions of mtDNA were first reported in muscle biopsy samples from patients suffering from a relatively common, sporadically occurring form of mitochondrial myopathy. In its severe and usually fatal form this disease is described as Kearns-Sayre syndrome (KSS), comprising muscle weakness, ataxia, pigmentary retinopathy, heart conduction block, ophthalmoplegia (paralysis of the eye muscles), deafness, and progressive dementia. The less severe variant of this disease (CPEO) usually comprises no more than chronic, progressive, external ophthalmoplegia. Partial duplications of mtDNA have also been observed in some severely affected patients and in these cases the rearranged molecules are detectable in blood.

Deletions have subsequently been reported in blood cell mtDNA of patients with Pearson's syndrome (a disease affecting pancreatic, spleen and blood functions), in heart muscle of patients with cardiomyopathy, and, more controversially, in the brains of patients with Parkinson's disease.

Deletions and duplications commonly involve apparent recombinational events, occurring between various pairs of short, directly repeated sequences in the genome, typically of 10–15 base pairs (bp). Although many such rearrangements have been found, a particular ("common") deletion of 5 kilobases (kb) is found in a significant minority (~35%) of KSS/CPEO patients. The mechanism of recombination could involve replication slippage, strand invasion, or protein-mediated strand exchange. Almost all such deletions preserve the separate origins of replication for each of the two strands leading to the suggestion that deleted molecules might be maintained by a replication advantage, even if they confer deleterious effects on the cell or organelle harboring them. Pathogenic rearrangements of mtDNA might also be generated, as in plants and fungi, by extragenomic mitochondrial plasmids.

Heritable rearrangements of mtDNA including a maternally inherited large deletion (removing the light strand origin, which is presumably replaced functionally by a cryptic origin elsewhere on the DNA strand) has been reported in a pedigree suffering from a syndrome comprising diabetes and deafness, but without muscle pathology. Point mutations of pathological significance have also been identified by sequence analysis of mtDNA from affected families and from many normal controls or, in some cases, by the chance occurrence of a restriction site polymorphism (RFLLP) as a result of the mutation. Such mutations are also commonly heteroplasmic and have been found to map to a variety of sites in the mitochondrial genome, including conserved amino acid residues of protein-coding genes, several tRNA genes, and also in potential regulatory regions, such as the attenuator sequence located downstream of the rRNA genes.

Each identified point mutation tends to be associated with a distinct, tissue-specific pathology. Thus, any one of a number of nonconservative substitutions in the genes for NADH dehydrogenase subunits 1 or 4 (ND1 or ND4) is found in association with Leber's hereditary optic neuropathy (LHON), a disease which is characterized by maternally inherited, bilateral, adult-onset blindness, resulting from optic nerve degeneration. A point mutation in the tRNALys gene correlates with the MERRF syndrome, a severe form of mitochondrial myopathy accompanied by myoclonic epilepsy.

Nuclear genes are also clearly involved in a number of these diseases. For example, familial cases of a KSS-like disease are associated with multiple deletions of mtDNA, but the predisposition to this condition is transmitted in a manner consistent with autosomal dominant inheritance. Nuclear mutations in fungi, which promote mitochondrial genomic instability, may provide an instructive model. In addition, LHON exhibits incomplete penetrance, with a significant sex bias suggestive of an X-linked component.

Defects in nuclear genes seem to be the predominant cause of some mitochondriopathies. Two likely examples are Leigh syndrome and Reye syndrome, each with a devastating (but quite distinct) encephalopathy, the latter also associated with hepatic failure. Reye syndrome manifests most commonly as an acute post-viral syndrome in children, and has been linked to the therapeutic use of aspirin. However, a very similar pathology has been reported in adults, associated with a generalized defect in intramitochondrial protein metabolism. The characteristic symptoms of Leigh syndrome (subacute necrotizing encephalomyelopathy) may also manifest in association with a defect in mitochondrial protein import and assembly, or alternatively as a result of a mitochondrial mutation. Leigh symptomology is found, for example, in severely affected members of a maternal pedigree carrying a (heteroplasmic) nonconservative substitution in the mitochondrial gene for subunit 6 of ATP synthase, a mutation which is minimally associated with a pathology of neurological ataxia and Retinitis Pigmentosa (NARP).

A deficiency of a fetal/neonatal isoform of a subunit of cytochrome c oxidase has been postulated as a cause of benign infantile mitochondrial myopathy, a transient pathology from which the affected infants usually make a complete recovery.

Mutant mitochondrial genomes have been successfully passaged from patient-derived cell lines to recipient cells of a different nuclear background, achieved by cytoplast fusion to a rhoO cell line depleted of mtDNA by prolonged growth in ethidium bromide. These experiments have demonstrated that abnormalities in the patterns of mitochondrial protein synthesis and/or in respiratory chain functions are determined by the mitochondrial genotype, at least for the point mutations associated with MERRF, MELAS, LHON and NARP.

Conditions in which the respiratory chain is affected are commonly associated with a characteristic muscle pathology, denoted as "ragged red fibers", and marked by accumulations of abnormal mitochondria often with paracrystalline inclusions, in the diseased fibres. This symptomology is seen with MERRF (hence its name), KSS/CPEO, and with another syndrome denoted MELAS (mitochondrial encephalomyopathy with lactic acidosis and stroke-like episodes), but is absent in LHON and NARP. It has been suggested that this muscle pathology may correlate with alterations to mtDNA which interfere in some way with the mitochondrial translational apparatus. These would include the tRNA point mutations seen in MERRF (in tRNALys) and MELAS (in tRNALeuURR), as well as the gross rearrangements found in KSS/CPEO, which would be predicted to lead to over- or under-representation of a variable number of tRNAs. The large deletion associated with diabetes and deafness is not associated with a muscle pathology, however.

The high mutation rate of mtDNA and the metabolic importance of its products suggest that it is an important mutational target in the aging process. Mitochondria are the main site of free radical generation in cells, and it has long been supposed that the most significant DNA damage is caused by such agents.

The use of a novel approach for specific detection of heteroplagmic mutations in mitochondrial DNA (mtDNA) has revealed high copy point mutations at specific positions in the control region of human cellular mtDNA from normal old, but not young individuals. Furthermore, longitudinal studies showed the appearance of the mutations in a given individual only at advanced age. Most dramatically, some mutations appeared in more than one individual. Thus, a T to G transvergion at position 414 was found, in a generally high proportion (up to 50%) of mtDNA molecules, in eight of 14 genetically unrelated individuals above 65 years of age, while it was absent in all 13 individuals younger than 65. These observations clearly point to and provide the first evidence of a large accumulation of, aging-dependent point mutations in mtDNA. Furthermore the occurrence of these mutations at sites critical for mtDNA replication and their abundance demonstrate their having a functional effect.

The idea that during mammalian cell aging there is an increasing incidence of mtDNA mutations (A. W. Linnane, S. Marzuki, T. Ozawa, M. Tanaka, Lancet 1,642 (1989), J. E. Fleming et al., Gerontology 28,44 (1982)) hag received, in the last ten years, support from direct experimental observations of an aging-related accumulation in this DNA of oxidative and alkylation derivatives of nucleotides and small deletions/insertions, and large deletions (C. Richter, J.-W. Park, B. N. Ames, Proc. Natl. Acad. Sci. U.S.A. 85, 6465 (1988); J.-W. Park, B. N. Ames, Proc. Natl. Acad. Sci. U.S.A. 85, 7467 (1988); L. Piko, A. T. Hougham, K. J. Bulpitt, Mech. Aging Dev. 43, 279 (1988); M. K. Shigenaga, T. M. Hagen, B. N. Ames, Proc. Natl. Acad. Sci. U.S.A. 91, 10771 (1994)). However, the low frequency of these mutations has raised questions about their functional significance. Furthermore, in contrast to the large deletions, the search for aging-dependent point mutations in human mtDNA has given inconclusive and often discordant results (F. Pallotti, X. Chen, E. Bonilla, E. A. Schon, Am. J. Hum. Genet. 59, 591 (1996)). This is in part due to the lack of a reliable method for detecting mutations which occur in heteroplasmic form, i.e., together with wild-type mtDNA, as expected for aging-related mutations, and to the search having been largely limited to the protein-and RNA-coding region of mtDNA. The main control region of mtDNA, which includes the D-loop and adjacent transcription promoters (DLP) (G. Attardi, Intern. Rev. Cytology 93,93 (1986)), is the most variable portion of the human mitochondrial genome (M. Hasegawa, S. Horai, J. Mol. Evol. 32, 37 (1991); M. Stoneking et al., Am. J. Hum. Genet. 48,370 (1991); T. J. Parsons et al., Nature Genet. 15,363 (1997)), in which heteroplasmic point mutations have also been reported (E. E. Jazin et al., hoc. Natl. Acad. Sci. U.S.A. 93, 12382 (1996)), and for which there is a higher probability of aging-related damage. Accordingly, the invention provides methods, compositions and kits for detecting, diagnosing and modulating age-dependent mutations in mtDNA.

As used herein and in the appended claims, the singular forms "a," "and," and "the" include plural referents unless the context clearly dictates otherwise. Thus, for example, reference to "a nucleic acid sequence" includes a plurality of sequences and reference to "the polynucleotide" generally includes reference to one or more polynucleotides and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference in full for the purpose of describing and disclosing the sequences and methodologies, which are described in the publications which might be used in connection with the invention described herein. The publications discussed above and throughout the text are provided solely for their disclosure prior to the filing date of the present application. Nothing herein is to be construed as an admission that the inventors are not entitled to antedate such disclosure by virtue of prior invention.

The headings and subheadings provided herein are provided solely for the convenience of the reader and are not to be construed to limit the invention.

Polynucleotides and Polypeptides

The term "isolated" means altered "by the hand of man" from its natural state; i.e., if it occurs in nature, it has been changed or removed from its original environment, or both. For example, a naturally occurring polynucleotide or a polypeptide naturally present in a living animal in its natural state is not "isolated", but the same polynucleotide or polypeptide separated from the coexisting materials of its natural state is "isolated", as the term is employed herein. As part of or following isolation, a polynucleotide can be joined to other polynucleotides, such as for example DNAs, for mutagenesis studies, to form fusion proteins, and for propagation or expression of the polynucleotide in a host. The isolated polynucleotides, alone or joined to other polynucleotides, such as vectors, can be introduced into host cells, in culture or in whole organisms. Such polynucleotides, when introduced into host cells in culture or in whole organisms, still would be isolated, as the term is used herein, because they would not be in their naturally occurring form or environment. Similarly, the polynucleotides and polypeptides may occur in a composition, such as a media formulation (solutions for introduction of polynucleotides or polypeptides, for example, into cells or compositions or solutions for chemical or enzymatic reactions which are not naturally occurring compositions) and, therein remain isolated polynucleotides or polypeptides within the meaning of that term as it is employed herein.

The term "oligonucleotide" as used herein is defined as a molecule comprised of two or more deoxyribonucleotides or ribonucleotides, preferably more than three, and usually more than ten. The exact size of an oligonucleotide will depend on many factors, including the ultimate function or use of the oligonucleotide. Oligonucleotides can be prepared by any suitable method, including, for example, cloning and restriction enzyme digestion of appropriate sequences and direct chemical synthesis by a method such as the phosphotriester method of Narang et al., 1979, Meth. Enzymol., 68:90–99; the phosphodiester method of Brown et al., 1979, Method Enzymol., 68:109–151, the diethylphosphoramidite method of Beaucage et al., 1981, Tetrahedron Lett., 22:1859–1862; the triester method of Matteucci et al., 1981, J. Am. Chem. Soc., 103:3185–3191, or automated synthesis methods; and the solid support method of U.S. Pat. No. 4,458,066.

"Polynucleotide" or "nucleic acid sequence" refers to a polymeric form of nucleotides at least 10 bases in length. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote. The nucleotides of the invention can be ribonucleotides, deoxyribonucleotides, or modified forms of either nucleotide. The term includes single- and double-stranded forms of DNA.

The terms polynucleotide(s) or oligonucleotide(s) generally refers to any ribonucleic acid or deoxyribonucleic acid sequence, which may be unmodified RNA or DNA or modified RNA or DNA. Thus, for instance, the nucleic acid sequences may be single-and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

The nucleic acid sequences described herein can contain one or more modified bases. Moreover, DNAs or RNAs comprising unusual bases, such as inosine, or modified bases, such as tritylated bases, to name just two examples, are nucleic acid sequences as the term is used herein.

It will be appreciated that a great variety of modifications have been made to DNA and RNA that serve many useful purposes known to those of skill in the art. The nucleic acid sequences as used herein embrace such chemically, enzymatically or metabolically modified forms of as well as the chemical forms of DNA and RNA characteristic of viruses and cells, including simple and complex cells, inter alia.

Nucleic acid sequences can be created which encode a fusion protein and can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns, maintenance of the correct reading frame of that gene to permit proper translation of the MRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A nucleic acid sequence of the invention includes, for example, a polynucleotide encoding a fusion protein, which may be inserted into a recombinant expression vector. The term "recombinant expression vector" refers to a plasmid, virus or other vehicle known in the art that has been manipulated by insertion or incorporation of a nucleic acid sequence of the invention. The expression vector typically contains an origin of replication, a promoter, as well as specific genes, which allow phenotypic selection of the transformed cells. Vectors suitable for use in the present invention include, but are not limited to the T7-based expression vector for expression in bacteria (Rosenberg, et al., Gene 56:125, 1987), the pMSXND expression vector for expression in mammalian cells (Lee and Nathans, J. Biol. Chem. 30 263:3521, 1988), baculovirus-derived vectors for expression in insect cells, cauliflower mosaic virus, CaMV; tobacco mosaic virug, TMV. The construction of expression vectors and the expression of genes in transfected cells involves the use of molecular cloning techniques also well known in the art. Sambrook et al., Molecular Cloning—A Laboratory Manual, Cold Spring Harbor Laboratory, Cold Spring Harbor, N.Y., 1989, and Current Protocols in Molecular Biology, M. Ausubel et al., eds., (Current Protocols, a joint venture between Greene Publishing Associates, Inc. and John Wiley & Sons, Inc., most recent Supplement). These methods include in vitro recombinant DNA techniques, synthetic techniques and in vivo recombination/genetic recombination. (See, for example, the techniques described in Maniatis, et al., Molecular Cloning A Laboratory Manual, Cold Spring Harbor Laboratory, N.Y., 1989).

In yeast, a number of vectors containing constitutive or inducible promoters may be used. For a review see, Current Protocols in Molecular Biology, Vol. 2, Ed. Ausubel, et al., Greene Publish. Assoc. & Wiley Interscience, Ch. 13, 1988; Grant, et al., "Expression and Secretion Vectors for Yeast," in Methods in Enzymology, Eds. Wu & Grossman, 1987, Acad. Press, N.Y., Vol. 153, pp. 516–544, 1987; Glover, DNA Cloning, Vol. II, IRL Press, Wash., D.C., Ch. 3, 1986; and Bitter, "Heterologous Gene Expression in Yeast," Methods in Enzymology, Eds. Berger & Kimmel, Acad. Press, N.Y., Vol. 152, pp. 673–684, 1987; and The Molecular Biology of the Yeast Saccharomyces, Eds. Strathem et al., Cold Spring Harbor Press, Vols. I and II, 1982. A constitutive yeast promoter such as ADH or LEU2 or an inducible promoter such as GAL may be used ("Cloning in Yeast," Ch. 3, R. Rothstein In: DNA Cloning Vol. 11, A Practical Approach, Ed. DM Glover, IRL Press, Wash., D.C., 1986). Alternatively, vectors may be used which promote integration of foreign DNA sequences into the yeast chromosome.

By "transformation" is meant a permanent (e.g., stable) or transient genetic change induced in a cell following incorporation of new DNA (i.e., DNA exogenous to the cell). Where the cell is a mammalian cell, a permanent genetic change is generally achieved by introduction of the DNA into the genome of the cell.

By "transformed cell" or "host cell" is meant a cell (e.g., prokaryotic or eukaryotic) into which (or into an ancestor of which) has been introduced, by means of recombinant DNA techniques a polynucleotide sequence of the invention or fragment thereof.

Transformation of a host cell may be carried out by conventional techniques as are well known to those skilled in the art. Where the host is prokaryotic, such as E. coli, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection include calcium phosphate co-precipitates, conventional mechanical procedures such as microinjection, electroporation, insertion of a plasmid encased in liposomes, or virus vectors, as well as others known in the art, may be used. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell may be a yeast cell (e.g., Saccharomyces cerevisiae), or may be a mammalian cell, including a human cell.

The term "primer" as used herein refers to an oligonucleotide, whether natural or synthetic, which is capable of acting as a point of initiation of synthesis when placed under conditions in which primer extension is initiated or possible. Synthesis of a primer extension product, which is complementary to a nucleic acid strand, is initiated in the presence of nucleoside triphosphates and a polymerase in an appropriate buffer at a suitable temperature. The term "primer" may refer to more than one primer, particularly in the case where there is some ambiguity in the information regarding one or both ends of the target region to be synthesized. For instance, if a nucleic acid sequence is inferred from a protein sequence, a "primer" generated to synthesize nucleic acid sequence encoding the protein sequence is actually a collection of primer oligonucleotides containing sequences representing all possible codon variations based on the degeneracy of the genetic code. One or more of the primers in this collection will be homologous with the end of the target sequence. Likewise, if a "conserved" region shows significant levels of polymorphism in a population, mixtures of primers can be prepared that will amplify adjacent sequences.

Polynucleotides

The invention provides nucleic acid sequences having a sequence corresponding to the H-strand initial replication portion of mitochondrial DNA. These nucleic acid sequences include DNA and RNA sequences, which correspond to the promoter for mtDNA H-strand primer synthesis and L-strand transcription (LSP), at a position immediately adjacent to a segment with high affinity for the mtTFA transcription factor (S. C. Ghivizzani et al., Molec. Cell. Biol. 14,7717 (1994))(FIG. 2C), and to positions related to mtDNA replication, in particular, either in the coding sequence of the RNA primer for H-strand synthesis, within mtTFA binding segments (S. C. Ghivizzani et al., Molec. Cell. Biol. 14:7717, 1994)), or very close to the $OH_{H1}$ primary site, or to the $O_{H2}$ secondary site of DNA synthesis initiation.

Specifically disclosed herein are polynucleotide sequences containing the mtDNA sequence(s) of the invention. An exemplary mtDNA polynucleotide sequence has the sequence as set forth in SEQ ID NO:1, wherein one or more of the following point mutations is present: T414G, A368G, a T insertion after position 383, T285C, A249G, T195C, T152C, T146C, variations in length or compositon of the homopolymer tract (HT) D310 at positions 303–315 or variations in length or composition of a CA repeat (positions 514–523), and combinations thereof.

The polynucleotides of the invention include SEQ ID NO:1, dominant negative forms of SEQ ID NO: 1, and nucleic acid sequences complementary to SEQ ID NO:1 wherein mutations at 514–523, 414, 383, 368, 303–313, 285, 249, 195, 152, 146, or combinations thereof are present (as described above). When the sequence is RNA, the deoxynucleotides A, G, C, and T of SEQ ID NO:1 are replaced by ribonucleotides A, G, C, and U, respectively. Also included in the invention are fragments of the above-described nucleic acid sequences that are at least 15 bases in length, which is sufficient to permit the fragment to specifically hybridize to polynucleotide sequence of SEQ ID NO:1 having mutations at 514–523, 414, 383, 368, 303–313, 285, 249, 195, 152, 146, or combinations thereof are present (as described above). The term "specifically hybridize" refers to hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions canbe used, e.g., for 10–15 minutes each, in the order listed above, repeating any or all of the steps listed. However, as mentioned above, optimal conditions will vary, depending on the particular hybridization reaction involved, and can be determined empirically.

Given the conservation of sequences between species, it would now be routine for one of skill in the art to obtain the mitochondrial nucleic acid sequence from any species, including those provided herein (i.e., human). For example, it is believed that other primate nucleic acid sequences are now readily obtainable using the sequences of the invention or fragments thereof as a probe. One of skill in the art can determine the percentage of sequence identity between species by aligning the polynucleotides, and then counting the number of bases shared between the sequences being compared at each aligned position. No penalty is imposed for the presence of insertions or deletions, but insertion or deletions are permitted only where required to accommodate an obviously increased number of amino acid residues in one of the sequences being aligned. Offsetting insertions just to improve sequence alignment are not permitted.

Percent identity is calculated for oligonucleotides of this length by not allowing gaps in the oligonucleotide for purposes of alignment. Methods to determine the homology and percent identity of sequences are well known in the art. These methods can be performed manually (using mathematical calculations) or with a computer program, such as BLAST (Altschul et al., 1986, Bull. Math. Bio. 48:603–616).

Homology can be measured using standard sequence analysis software (e.g., Sequence Analysis Software Package of the Genetics Computer Group, University of Wisconsin Biotechnology Center, 1710 University Avenue, Madison, Wis. 53705; also see Ausubel, et al., supra). Such procedures and algorithms include, for example, a BLAST program Basic Local Alignment Search Tool at the National Center for Biological Information), ALIGN, AMAS (Analysis of Multiply Aligned Sequences), AMPS (Protein Multiple Sequence Alignment), ASSET (Aligned Segment Statistical Evaluation Tool), BANDS, BESTSCOR, BIOSCAN (Biological Sequence Comparative Analysis Node), BLIMPS (BLocks IMProved Searcher), FASTA, Intervals & Points, BMB, CLUSTAL V, CLUSTAL W. CONSENSUS, LCONSENSUS, WCONSENSUS, Smith-Waterman algorithm, DARWIN, Las Vegas algorithm, FNAT (Forced Nucleotide Alignment Tool), Framealign, Framesearch, DYNAMIC, FILTER, FSAP (Fristensky Sequence Analysis Package), GAP (Global Alignment Program), GENAL, GIBBS, GenQuest, ISSC (Sensitive Sequence Comparison), LALIGN (Local Sequence Alignment), LCP (Local Content Program), MACAW (Multiple Alignment Construction & Analysis Workbench), MAP (Multiple Alignment Program), MBLKP, MBLKN, PIMA (Pattern-Induced Multi-sequence Alignment), SAGA (Sequence Alignment by Genetic Algorithm) and WHAT-IF. Such alignment programs can also be used to screen genome databases to identify polynucleotide sequences having substantially identical sequences. A number of genome databases are available, for example, a substantial portion of the human genome is available as part of the Human Genome Sequencing Project (J. Roach, http://weber.u.Washington.edu/~roach/human_genome_progress2.html) (Gibbs, 1995). At least twenty-one other genomes have already been sequenced, including, for example, *M. genitalium* (Fraser et al., 1995), *M. jannaschii* (Bult et al., 1996), *H. influenzae* (Fleischmann et al., 1995), *E. coli* (Blattner et al., 1997), and yeast (*S. cerevisiae*) (Mewes et al., 1997), and *D. melanogaster* (Adams et al., 2000). Significant progress has also been made in sequencing the genomes of model organism, such as mouse, *C. elegans*, Arabadopsis sp. and *D. melanogaster*. Several databases containing genomic information annotated with some functional information are maintained by different organization, and are accessible via the internet, for example, http://wwwtigr.org/tdb; http://www.genetics.wisc.edu; http://genome-www.stanford.edu/ ~ball; http://hiv-web.lanl.gov; http://www.ncbi.nlm.nih.gov; http://www.ebi.ac.uk; http://Pasteur.fr/other/biology; and http://www.genome.wi.mit.edu.

Diagnostics

The heteroplasmy associated with the mitochondrial genome poses a major challenge in designing a DNA-based diagnostic test. Sequencing of the H-strand sequence which play a role in replication revealed the existence of a mitochondrial DNA molecule that contains a number of transversion and insertion mutations. In addition, sequencing studies suggest an elevated mutational burden in aged subjects that may be associated with impaired cellular energy metabolism and disease phenotypes. Therefore, a critical requirement to improved genetic detection of such age-related disorders is the quantitation of mitochondrial DNA (mtDNA) heteroplasmy. When applicable, the methods often require tailored optimization conditions for interrogating each mutation site for efficient discrimination of wild-type and mutant alleles. Mutation analysis by restriction fragment length polymorphism (RFLP) is best applicable when mutations cause a gain or loss of a restriction site. However, the technique lacks sensitivity for detecting mutant alleles which appear at low frequencies.

In one embodiment, the invention provides methods to identify mitochondrial associated disorders or age dependent mutations in a subject by amplifying highly enriched mitochondrial nucleic acid fractions with primers specific to a region to be analyzed and analyzing the amplified products to identify amplification products that are different from a control.

Mitochondrial nucleic acids are enriched by subcellular fractionation of a cell sample. Such methods are known in the art and are based on the relative density of cellular organelles. Nucleic acids can be obtained from these fractions by standard techniques. The mitochondrial nucleic acids can then be further enriched by removing nucleic acid sequences that are not mitochondrial in origin. This uses the process of selective nuclease digestion of the nucleic acids present in a sample. Certain nucleases do not digest human mitochondrial DNA sequences and thus act specifically on nuclear DNA sequences. Such nucleases are known in the art and include, for example, BglII, DraIII. Other nuclease can be used such as ribonuclease A (RNase A) and Exonuclease III (all of which are commercially available).

The highly enriched fraction of mitochondrial DNA can then subjected to nucleic acid amplification to amplify a target sequence of interest. A target sequence of interest is any sequence or loci that may be linked to a disorder or disease or associated with a mutation. In addition to the novel age related mutations, identified herein, other loci or alleles related to particular diseases or disorders are known in the art. Accordingly, the target sequence or allele is amplified using any number of techniques including the polymerase chain reaction (PCR). For example, using primer sequences flanking the target sequence, a sufficient number of PCR cycles are performed to provide an amplified product corresponding to the target sequence or allele.

The target sequences or alleles are tested for the presence of a nucleic acid sequence different from the normal allele by determining the nucleotide sequence of the cloned allele or amplified fragment and comparing it to the nucleotide sequence of the normal allele. There are a number of methods that can be used to determine sequence differences. Six well known methods for confirming the presence of a predisposing allele include, for example, 1) single stranded conformation analysis (SSCA) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the *E. coli* mutS protein (Modrich, 1991); and, 6) allele-specific PCR (Rano & Kidd, 1989). For allele-specific PCR, primers are used which hybridize at their 3' ends to a particular mutations. If the particular mutation is not present, an amplification product is not observed. Amplification Refractory Mutation System (ARMS) can also be used, as disclosed in European Patent Application Publication No. 0332435 and in Newton et al., 1989.

In the first three methods (SSCA, DGGE and RNase protection assay), a new electrophoretic band appears. SSCA detects a band that migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Denaturing gradient gel electrophoreis is based on the melting behavior of the DNA fragments and the use of denaturing gradient gelelectrophoresis as shown by Fischer, S. G. and Lerman, L. S. (1983) Proc. Natl. Acad. Sci. U.S.A. 80: 1579–83; Myers, R. M., Fischer, S. G., Maniatis, T. and Lerman, L. S. (1985) Nucl. Acids Res. 13: 3111–3129; Lerman, L. S., Silverstein, K. and Grinfeldt, E. in Molecular Biol. of Homo Sapiens, Cold Spring Harbor Lab. (1986) pp. 285–297. DNA fragients differing by single base substitutions can be separated from each other by electrophoresis in polyacrylamide gels containing an ascending gradient of the DNA denaturants urea and formamide. Two identical DNA fragments differing by only one single base pair, will initially move through the polyacrylamide gel at a constant rate. As they migrate into a critical concentration of denaturant, specific domains within the fragments melt to produce partially denatured DNA. Melting of a domain is accompanied by an abrupt decrease in mobility. The position in the denaturant gradient gel at which the decrease in mobility is observed corresponds to the melting temperature of that domain. Since a single base substitution within the melting domain results in a melting temperature difference, partial denaturation of the two DNA fragments will occur at different positions in the gel. DNA molecules can therefore be separated on the basis of very small differences in the melting temperature. Additional improvements to this DGGE have been made as disclosed by Borresen in U.S. Pat. No. 5,190,856.

In addition, after a first DGGE analysis, an identified product can be cloned, purified and analyzed a second time by DGGE.

In another embodiment, a nucleic acid probe specific for SEQ ID NO: 1 having any one or more the mutations described above may be used to detect polynucleotide (using nucleic acid probe) in subject samples such as biological fluids, cells, fractionated cells (e.g., organelle preparations), tissues, or nucleic acid. Any specimen containing a detectable amount of a polynucleotide can be used, Examples of biological fluids of use with the invention are blood, serum, plasma, urine, mucous, and saliva. Tissue or cell samples can also be used with the subject invention. The samples can be obtained by many methods such as cellular aspiration, or by surgical removal of a biopsy sample.

The nucleic acid probe is preferably labeled with a compound which allows detection of binding to a polynucleotide sequence in the sample. The level of the polynucleotide in the subject cell can be compared with the level in a cell not having a mutated mtDNA sequence. Preferably the subject is human.

The polynucleotides of the invention can be used in vitro and in vivo to monitor the course of or degree of mutation in the DNA (e.g., mtDNA) in a subject.

Mutational analysis can also be carried out by methods based on ligation of oligonucleotide sequences which anneal immediately adjacent to each other on a target DNA or RNA molecule (Wu and Wallace, Genomics 4: 560–569 (1989); Landren et al., Science 241: 1077–1080 (1988); Nickerson et al., Proc. Natl. Acad. Sci. 87: 8923–8927 (1990); Barany, F., Proc. Natl. Acad. Sci. 88: 189–193 (1991)). Ligase-mediated covalent attachment occurs only when the oligonucleotides are correctly base-paired. The Ligase Chain Reaction (LCR) and the oligonucleotide ligation assay (OLA), which utilize the thermostable Tag ligase for target amplification, are particularly useful for interrogating mutation loci. The elevated reaction temperatures permit the ligation reaction to be conducted with high stringency (Barany, F., PCR Methods and Applications 1: 5–16 (1991)) (Grossman, P. D. et al., Nucl. Acids. Res. 22: 4527–4534, (1994)).

Analysis of point mutations in DNA can also be carried out by using the polymerase chain reaction (PCR) and variations thereof. Mismatches can be detected by competitive oligonucleotide priming under hybridization conditions where binding of the perfectly matched primer is favored (Gibbs et al., Nucl. Acids. Res. 17: 2437–2448 (1989)). In the amplification refractory mutation system technique (ARMS), primers can be designed to have perfect matches or mismatches with target sequences either internal or at the 3' residue (Newton et al., Nucl. Acids. Res. 17: 2503–2516 (1989)). Under appropriate conditions, only the perfectly annealed oligonucleotide can function as a primer for the PCR reaction, thus providing a method of discrimination between normal and mutant sequences.

Detection of single base mutations in target nucleic acids can be conveniently accomplished by differential hybridization techniques using sequence-specific oligonucleotides (Suggs et al., Proc. Natl. Acad. Sci. 78: 6613–6617 (1981); Conner et al., Proc. Natl. Acad. Sci. 80: 278–282 (1983); Saiki et al., Proc. Natl. Acad. Sci. 86: 6230–6234 (1989)). Mutations can be diagnosed on the basis of the higher thermal stability of the perfectly matched probes as compared to the mismatched probes. The hybridization reactions can be carried out in a filter-based format, in which the target nucleic acids are immobilized on nitrocellulose or nylon membranes and probed with oligonucleotide probes. Any of the known hybridization formats may be used, including Southern blots, slot blots, "reverse" dot blots, solution hybridization, solid support based sandwich hybridization, bead-based, silicon chip-based and microtiter well-based hybridization formats.

An alternative strategy involves detection of the mutant sequences by sandwich hybridization methods. In this strategy, the mutant and wildtype (normal) target nucleic acids are separated from non-homologous DNA/RNA using a common capture oligonucleotide immobilized on a solid support and detected by specific oligonucleotide probes tagged with reporter labels. The capture oligonucleotides can be immobilized on microtitre plate wells or on beads (Gingeras et al., J. Infect. Dis. 164: 1066–1074 (1991); Richman et al., Proc. Natl. Acad. Sci. 88: 11241–11245 (1991)).

Another method for analysis of a biological sample for specific mutations in the mtDNA (e.g., mutants of SEQ ID NO:1 or a fragment thereof) sequence is a multiplexed primer extension method. In this method primer is hybridized to a nucleic acid suspected of containing a mutation such that the primer is hybridized 3' to the suspected mutation. The primer is extended in the presence of a mixture of one to three deoxynucleoside triphosphates and one of three chain terminating deoxynucleoside triphosphates selected such that the wild-type extension product, the mutant DNA-derived extension product and the primer each are of different lengths. These steps can be repeated, such as by PCR or RT-PCR, and the resulting primer extended products and primer are then separated on the basis of molecular weight to thereby enable identification of mutant DNA-derived extension product.

The multiplexed primer extension method may also be used to analyze the heteroplasmy of multiple genetic mutations relative to corresponding wild-type sequences within a sample. In this method, two or more differentiable primers to a nucleic acid suspected of having genetic mutations are hybridized 3' to the location of the suspected mutations. The primers are extended in the presence of a mixture of one to three deoxynucleoside triphosphates and one to three chain terminating deoxynucleoside triphosphates such that for each of the two or more differentiable primers, the corresponding wild-type extension product and the corresponding mutant DNA-derived product differ in length from each other and the primer. After several rounds of extension the products are separated on the basis of molecular weight and mutant DNA extension products identified. Typically, a high fidelity DNA polymerase is used in the extension reactions.

While radio-isotopic labeled detection oligonucleotide probes are highly sensitive, non-isotopic labels can also be used due to concerns about handling and disposal of radioactivity. A number of strategies are available for detecting target nucleic acids by non-isotopic means (Matthews et al., Anal. Biochem., 169: 1–25 (1988)). The non-isotopic detection method can be direct or indirect.

The indirect detection process generally involves the use of an oligonucleotide probe that is covalently labeled with a hapten or ligand, such as digoxigenin (DIG) or biotin, for example. Following the hybridization step, the target-probe duplex is detected by an antibody- or streptavidin-enzyme complex. Enzymes commonly used in DNA diagnostics are horseradish peroxidase and alkaline phosphatase. One particular indirect method, the GENIUS detection system (Boehringer Mannheim) is especially useful for mutational analysis of the mitochondrial DNA. This indirect method uses digoxigenin as the tag for the oligonucleotide probe and is detected by an anti-digoxigenin-antibody-alkaline phosphatase conjugate.

Direct detection methods include the use of fluorophor-labeled oligonucleotides, lanthanide chelate-labeled oligonucleotides or oligonucleotide-enzyme conjugates. Examples of fluorophor labels are fluorescein, rhodamine and phthalocyanine dyes. Examples of lanthanide chelates include complexes of $Eu^{3+}$ and $Tb^{3+}$. Directly labeled oligonucleotide-enzyme conjugates are preferred for detecting point mutations when using target-specific oligonucleotides as they provide very high sensitivities of detection.

Oligonucleotide-enzyme conjugates can be prepared by a number of methods (Jablonski et al., Nucl. Acids Res., 14: 6115–6128 (1986); Li et al., Nucl. Acids. Res., 15: 5275–5287 (1987); Ghosh et al., Bioconjugate Chem. 1: 71–76 (1990)), and alkaline phosphatase is the enzyme of choice for obtaining high sensitivities of detection. The detection of target nucleic acids using these conjugates can be carried out by filter hybridization methods or by bead-based sandwich hybridization (Ishii et al., Bioconjugate Chemistry 4: 34–41 (1993)).

Detection of the probe label can be accomplished by the following approaches. For radioisotopes, detection is by autoradiography, scintillation counting or phosphor imaging. For hapten or biotin labels, detection is with antibody or streptavidin bound to a reporter enzyme such as horseradish peroxidase or alkaline phosphatase, which is then detected by enzymatic means. For fluorophor or lanthanide-chelate labels, fluorescent signals can be measured with spectrofluorimeters with or without time-resolved mode or using automated microtitre plate readers. With enzyme labels, detection is by color or dye deposition (p-nitrophenyl phosphate or 5-bromo-4-chloro-3-indolyl phosphate/nitroblue tetrazolium for alkaline phosphatase and 3,3'-diaminobenzidine-$NiCl_2$ for horseradish peroxidase), fluorescence (e.g. 4-methyl umbelliferyl phosphate for alkaline phosphatase) or chemiluminescence (the alkaline phosphatase dioxetane substrates LumiPhos 530 from Lumigen Inc., Detroit, Mich. or AMPPD and CSPD from Tropix, Inc.). Chemiluminescent detection can be carried out with x-ray or polaroid film or by using single photon counting luminometers. This is the typical detection format for alkaline phosphatase labeled probes.

In one aspect of the invention, the oligonucleotide ligation assay (OLA) is applied for quantitative mutational analysis of mitochondrial DNA. In this embodiment of the invention, a thermostable ligase-catalyzed reaction is used to link a fluorescently labeled common probe with allele-specific probes. The latter probes are sequence-coded with non-nucleotide mobility modifiers which confer unique electrophoretic mobilities to the ligation products. The oligonucleotide ligation assay is described in detail in Grossman, et al. (1994), Nuc. Acids Res. 22: 4527–4534, incorporated herein in its entirety by reference thereto.

Normal and mutant probes are synthesized with different oligomeric nucleotide or non-nucleotide modifier tails at their 5' termini. Examples of nucleotide modifiers are inosine or thymidine residues, whereas examples of non-nucleotide modifiers include pentaethyleneoxide (PEO) and hexaethyleneoxide (HEO) monomeric units. The non-nucleotide modifiers are preferred and most preferably, PEO is used to label the probes. When a DNA template is present, a thermostable DNA ligase catalyzes the ligation of normal and mutant probes to a common probe bearing a fluorescent label. The PEO tails modify the mobilities of the ligation products in electrophoretic gels. The combination of PEO tails and fluorophor labels (TET and FAM (5-carboxy-fluorescein derivatives)), HEX and JOE (6-carboxy-fluorescein derivatives), ROX (6-carboxy-x-rhodamine), or TAMRA (N, N, N', N'-tetramethyl-6-carboxy-rhodamine), for example, which are available from Perkin-Elmer, ABI Division, Foster City, Calif. permit multiplexing based on size and color by providing unique electrophoretic signatures to the ligation products. The products are separated by electrophoresis, and fluorescence intensities associated with wild-type and mutant products are used to quantitate heteroplasmy. Thus, wild-type and mutant sequences are detected and quantitated on the basis of size and fluorescence intensities of the ligation products. Importantly, this method may be configured for quantitative detection of multiple age-associated mutations in a single ligation reaction.

For quantitative analysis of age-associated mutations using OLA, oligonucleotide probes are preferably labeled with fluorophor labels that provide spectrally distinguishable characteristics. In one embodiment, oligonucleotides are labeled with 5' oligomeric pentaethyleneoxide (PEO) tails. Synthesis of such 5' labeled oligonucleotides can be carried out, for example, using an automated synthesizer using standard phosphoramidite chemistry. Following cleavage from resin and deprotection with ammonium hydroxide, the $(PEO)_n$-oligonucleotides may be purified by reverse phase HPLC. Oligonucleotides with 3'-FAM or TET dyes (Perkin Elmer) and 5'-phosphates may be synthesized and purified by the procedure of Grossman, et al., (1994), Nucl. Acids Res., 22: 4527–4534.

The 5'-PEO-labeled probes may be synthesized to have 5'-PEO-tails of differing lengths to facilitate distinguishing the ligated probe products both electrophoretically by size and by spectral characteristics of the fluorophor labels.

The oligonucleotide probes are used for interrogating age-associated mutations, preferably at one or more mtDNA nucleotide positions 514–523, 414, 383, 368, 303–313, 285, 249, 195, 152, 146, or combinations thereof are present (as described above). The oligonucleotide probes for the OLA assay are typically designed to have calculated melting temperatures of about 40° C. to 50° C., most typically about 48° C. by the nearest neighbor method (Breslaur, et al., (1986), Proc. Natl. Acad. Sci. U.S.A., 83: 9373–9377) so that the ligation reaction may be performed at a temperature range of about 40° C. to 60° C., typically from about 45° C. to about 55° C. The wild-type, mutant and common oligonucleotide probes are preferably synthesized with various combinations of pentaethyleneoxide (PEO) oligomeric tails and fluorescein dyes, such as TET and FAM. These combinations of mobility modifiers and fluorophor labels furnish electrophoretically unique ligation products that can enable more than one of the age-associated nucleotide sites to be monitored in a single ligation reaction.

Also contemplated are methods to modulate a mitochondrial control region, for example, by introducing one or more of the mutations to SEQ ID NO:1 as described above (e.g., T414G, A368G, a T insertion after position 383, T285C, A249G, T195C, T152C, T146C, variations in length or compositon of the homopolymer tract (HT) D310 at positions 303–315 or variations in length or composition of a CA repeat (positions 514–523), and any combination thereof) into a mitochondrial DNA control region of a eukaryotic cell or a mammalian subject. Alternatively, it is possible to modulate the control region having one or more of the foregoing mutations by introducing a wild type mitochondrial sequence or modifying the control region sequence of a mutated mitochondrial sequence in order to produce a wild type sequence. Such methods include the use of vectors and sequences capable of directing a polynucleotide sequence to a mitochondrial organelle. For example, using DNA coupled covalently to a short mitochondrial leader peptide (chimera) can enter mitochondria via the protein import pathway. These methods provide a way for gene-, antisense-RNA or antisense-DNA-delivery in molecular therapies specifically directed to the mitochondria of a cell (see, for example, Seibel et al. Nucleic Acids Res. 23:10–17, 1995, the disclosure of which is incorporated by reference herein). Such chimera can be engineered to be delivered to a subject by recombinant vectors as described above (e.g., AAV vectors or retroviral vectors) containing a sequence of the invention. Another method to deliver a therapeutic sequence or to introduce a nucleic acid sequence of the invention includes the use of high velocity microprojectile bombardment. Such bombardment methods are currently used to introduce polynucleotide sequences into mitochondrial organelles (see, for example, Wiesenberger et al., Mol. Cel. Biol. 15:3291–3300, 1995; Bonnefoy and Fox, Mol. Gen. Genet., 262:1036–1046, 2000, the disclosures of which are incorporated by reference herein). While not wanting to be bound by any theory the methods described above can be achieved by in vivo recombination with the mtDNA. Accordingly, the invention contemplates methods to deliver therpeutic sequence to a subject by nucleic acid delivery techniques known in the art. Such therpeutic sequences include the sequences of the invention.

Kits

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe which is or can be detectably labeled. Such probe may be a nucleic acid sequence specific SEQ ID NO:1 having one or more of the mutations described above (e.g., T414G, A368G, a T insertion after position 383, T285C, A249G, T195C, T152C, T146C, variations in length or compositon of the homopolymer tract (HT) D310 at positions 303–315 or variations in length or composition of a CA repeat (positions 514–523)) or specific fragments thereof. For example, oligonucleotide probes of the invention can be included in a kit and used for examining the presence of mutated mtDNA in a sample, as well as the quantitative (relative) degree of binding of the probe for determining the occurrence of specific strongly binding (hybridizing) sequences, thus indicating the likelihood for a subject having or predisposed to a disorder associated with aging.

The kit may also contain a container comprising a reporter-means, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the mutant target sequence, this can be accomplished using oligonucleotide(s) that are primers for amplification. These oligonucleotide primers are based upon identification of the flanking regions contiguous with the target nucleotide sequence.

The invention will now be described in greater detail by reference to the following non-limiting examples.

EXAMPLES

Work involving transfer of mitochondria from fibroblasts of differently aged individuals into mtDNA-less (p°)cells had shown a very significant aging-dependent decline in the mtDNA content of the clones (K. A. Laderman et al., J. Biol. Chem. 271,15891 (1996)). The invention has identified that the main mtDNA control region and, in particular, the segment which contains the critical control sequences for mtDNA replication demonstrates age dependent mtDNA mutation. For this purpose, a novel approach for the specific detection of heteroplasmic mtDNA mutations was developed. This approach has a sensitivity that allows the identification of as low a proportion of mutant mtDNA as 2–4%, at the same time excluding any interference by nuclear mtDNA pseudogenes which tend to produce false positives (M. Hirano et al., Proc. Natl. Acad. Sci. U.S.A. 94, 14894 (1997); D. C. Wallace et al., Proc. Natl. Acad. Sci. U.S.A. 94, 14900 (1997); B. Parfait, P. Rustin, A. Murnick, A. R ötig, Biochem. Biophys. Res. Commun. 247, 57 (1998)). This approach is based on the use of mtDNA highly purified by cell fractionation and enzyme digestion, and of a very sensitive denaturant gradient gel electrophoresis (DGGE) technique for identification of even single nucleotide mismatches in artificially produced heteroduplexes (Y. Michikawa, G. Hofhaus, L. S. Lerman, G. Attardi, Nucl. Acid Res. 25, 2455 (1997)), combined with cloning, second-round DGGE and sequencing. An mtDNA-less cell line (M. P. King, G. Attardi, Science 246, 500 (1989)) was used as a negative control. For DGGE analysis, the main mtDNA control region, based on the mtDNA sequence having GenBank Accession No. V0062 (which is incorporated herein by reference), was subdivided into seven segments, 160 to 440 bp in length (DLP1 to DLP7), each with a single uniform melting domain (FIG. 2A). For this purpose, the computer program MELT94 (L. S. Lerman et al.http://wcb.mit.edu/osp/www/melt.html) was used. The chosen primer oligodeoxynucleotides, one of which carried a psoralen clamp, substituting for a GC clamp (R. M. Myers, S. G. Fischer, T. Maniatis, L. S. Lerman. Nuel. Acids Res. 13, 3111 (1985)), were synthesized with an Applied Biosystems 394 apparatus (ABI, Foster City, Calif.), as detailed in Y. Michikawa, G. Hofhaus, L. S. Lerman, G. Attardi, Nucl. Acid Res. 25, 2455 (1997). The two segments DLP4 and DLP6 were used for this investigation. These two segments contain the control sequences for mtDNA heavy (H)-strand synthesis initiation, and correspond to one of the hypervariable portions of the main control region, exhibiting a high frequency of inter-individual polymorphisms (B. D. Greenberg, J. E. Newbold, A. Sugino, Gene 21,33 (1983)). DLP4 contains the primary origin of H-strand mtDNA synthesis ($O_{H1}$), while DLP6 contains the two evolutionarily conserved sequence blocks CSB2 and CSB3 (M. W. Walberg, D. A. Clayton, Nucl. Acids Res. 9,5411 (1981)) and the start site for light (L)-strand transcription and H-strand RNA primer synthesis (J. Montoya et al., Proc. Natl. Acad. Sci. U.S.A. 79,7195 (1982)). The block CSB2 carries the homopolymeric tract (HT)D310, a sequence of 12 to 18 C's interrupted by a T at position 310 (W. W. Hauswirth, D. A. Clayton, Nucl. Acids Res. 13,8093 (1985)), which exhibits length variation among individuals (B. D. Greenberg, J. E. Newbold, A. Sugino, Gene 21,33 (1983); S. Anderson et al., Nature 290,457 (1981)) and also heteroplasmic variation within an individual (E. E. Jazin et al., hoc. Natl. Acad. Sci. U.S.A. 93, 12382 (1996); D. R. Marchington, G. M. Hartshorne, D. Barlow, J. Poulton, Am. J. Hum. Genet. 60, 408 (1997)).

Figure 1B:
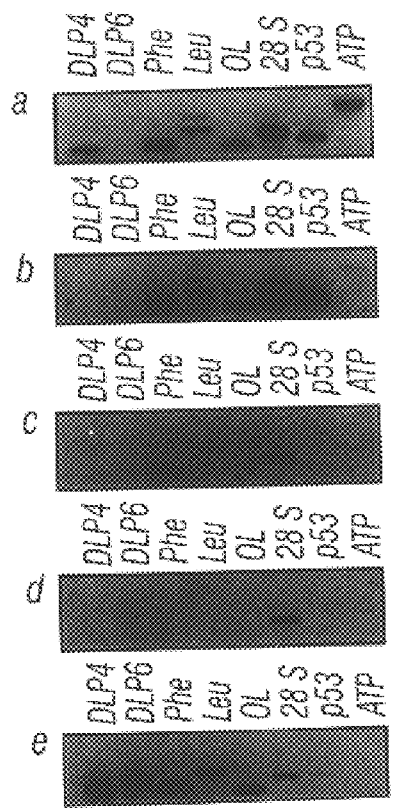
Figure 1C:
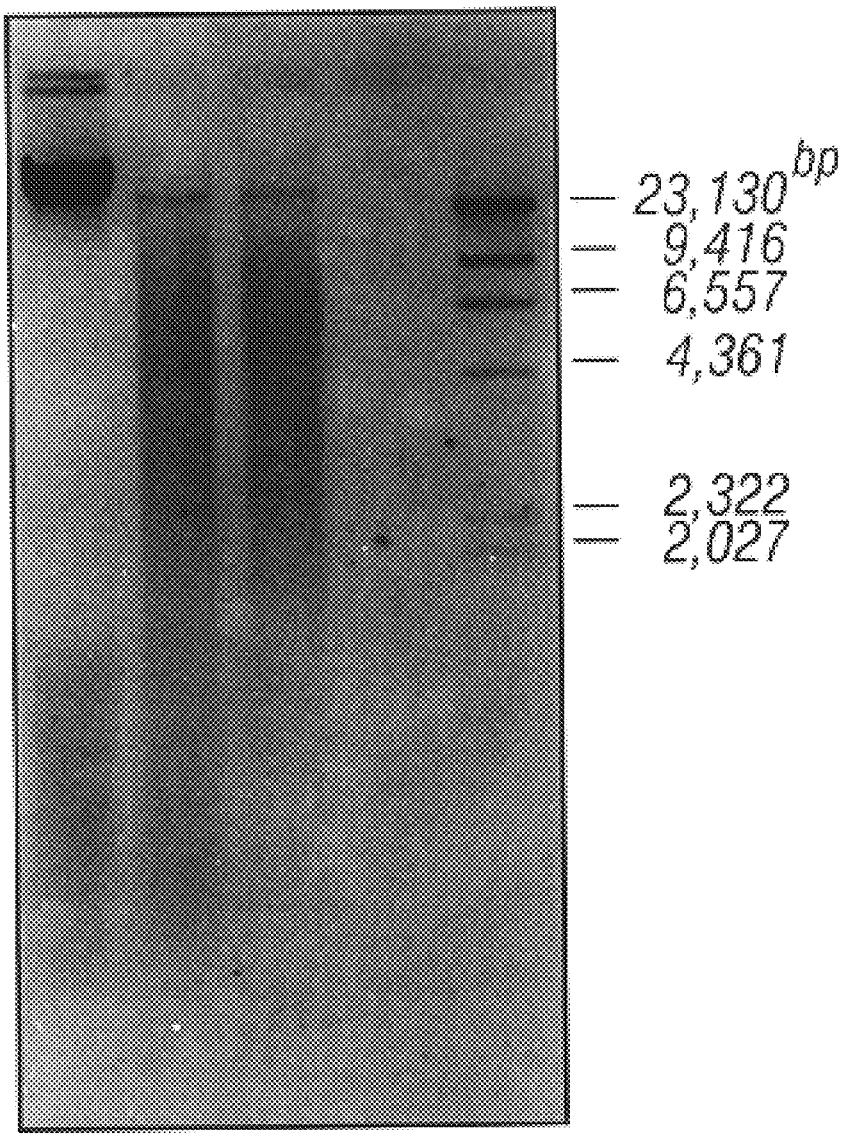

To evaluate the role of nuclear mtDNA pseudogenes in yielding PCR products with mtDNA-specific primers, total DNA from the mtDNA-less cell line zhoO 206 (M. P. King, G. Attardi, Science 246, 500 (1989)) was tested with primers specific for the mtDNA DLP4 and DLP6 segments, for two mitochondrial tRNA genes (tRNA$^{Phe}$, tRNA$^{Leu(UUR)}$), for the region containing the origin of mtDNA L-strand synthesis (OL), and, as a control, for three nuclear genes, i.e., those for the 28s rRNA, the p53 and the ATPase α-subunit. Cells of the 143B TK-mtDNA-less derivative zhoO 206 were grown, and total cell DNA was isolated by the standard proteinase K/sodium dodecyl sulfate (SDS) treatment, followed by phenol/chloroform extraction. mtDNA was isolated by cell homogenization, treatment of the pelleted mitochondrial fraction with micrococcal nuclease (Worthington) to digest contaminating nuclear DNA and nucleocytosolic RNA (S. Crews, and G. Attardi, Cell 19, 775 (1981)), followed by extraction by the proteinase K/SDS-phenol/chloroform procedure. To destroy completely the nuclear DNA and the nucleocytosolic RNA present, both the total cell DNA preparation and the mtDNA preparation were sequentially treated, each step being carried out for 2 h at 37° C., with a mixture of two restriction enzymes which do not cut human mtDNA (BglII and DraIII, New England Biolabs (F. Vaillant and P. Nagley, Hum. Mol. Genet. 4, 903, 1995)), with RNase A (Sigma), unless otherwise specified, and with Exonuclease III (Worthington), in a medium containing 50 mM Tris/HCl (pH 7.9 at 25° C.), 10 mM MgCl$_2$, 100 mM NaCl and 1 mM dithiothreitol. As shown in FIG. 1C, prior to the enzyme treatment, the nuclear DNA present in the total cell DNA sample migrated in an agarose gel as a band moving more slowly than the 23.1 kb λ DNA HindIII fragment, and the heterogeneous RNA migrated faster than the 2 kb λ DNA fragment. After the three digestion steps, no ethidium bromide-stained material was recognizable in the gel. For amplification of the DLP4 and DLP6 mtDNA segments, primer pairs corresponding to positions 111–132 and 271–253 and, respectively, 261–280 and 541–524 were used. The PCR primers for mitochondrial tRNA$^{Phe}$, tRNA$^{Leu(UUR)}$ and OL were as described in Y. Michikawa, G. Hofhaus, L. S. Lerman, G. Attardi, Nucl. Acid Res. 25, 2455 (1997). Appropriate primers were used for amplification of the human p53, 28S rRNA and ATPase α-subunit genes. The PCR amplification reactions, using a DNA Thermal Cycler 480 (Perkin Elmer) and the Expand™ High Fidelity PCR System (Boehringer Mannheim), and the optimization of the MgCl$_2$ concentration were carried out as described (Y. Michikawa, G. Hofhaus, L. S. Lerman, G. Attardi, Nucl. Acid Res. 25, 2455 (1997)). PCR products were obtained with primers for the three nuclear genes, and, more significantly, also with primers for the two mitochondrial tRNA genes, for OL, and, in small amounts, for DLP4 (FIG. 1Ba). These results pointed to the presence of nuclear pseudogenes corresponding to these mtDNA segments in zhoO 206 cells.

Using as a template total DNA from zhoO 206 cells, in which nuclear DNA and nucleo-cytosolic RNA had been nearly completely digested with BglII, DraIII, RNase A and ExoIII (FIG. 1C), products were still obtained with the primers for the 28S rRNA, p53 and ATPase α-subunit genes, as well as for the two mitochondrial tRNA genes and OL, but no products with the primers for DLP4 and DLP6 (FIG. 1Bb). In further tests, DNA extracted from the micrococcal nuclease (MN)-treated mitochondrial fraction of zhoO 206 cells yielded products only with primers for the tRNAPhe, p53 and 28S rRNA genes (FIG. 1Bc). On the contrary, after digestion with BglII, DraIII and ExoIII, the same DNA yielded only products of 28S rRNA genes, presumably reflecting the very large number of copies of these genes (FIG. 1Bd). mtDNA purified in the same way from fibroblasts of a 19 year-old individual also yielded, besides the expected PCR amplification products of the five mtDNA segments tested, a small amount of 28s rRNA gene products (FIG. 1Be). MtDNA purified as last described was used for all the analyses below.

The PCR products of the DLP4 and DLP6 segments of untreated total cell DNA and highly purified mtDNA from fibroblast cultures of 18 randomly chosen, genetically unrelated normal individuals between 20 week-fetal (20 wf) and 101 years in age and of nine normal individuals twice-sampled, with a 9-to 19-year interval, for the Gerontology Research Center (N. I. H.) longitudinal study (LS) were subjected to first-DGGE analysig. Skin fibroblatg from normal Caucasian individuals of varying age (from 20-week fetal to 101 years) were either obtained from the NIGMS Human Genetic Mutant Cell Repository (Camden, N.J.)(20 wf, 1 y, 10 y, 13 y, 19 y, 24 y, 25 y, 26 y, 42 y, 48 y, 78-1 y, 98 y), or from the National Institute of Aging Cell Respository (Camden, N.J.)(nine twice-sampled longitudinal study (LS)individuals (LS1 (52 y-71 y), LS2 (59 y-75 y), LS3 (63 y-78-2 y), LS4 (64 y-80 y), LS5 (65 y-74-1 y), LS6 (66 y-82 y), LS7 (70 y-86-2 y), LS8 (73 y-89y), LS9 (77 y-90 y))and 74-2 y), or from the Institute of Clinical Neurology of the University of Milan, Italy (86-1 y, 100-1 y, 100-2 y, 100-3 y, 101 y). The latter sets of individuals, all from retirement homes, were free of any neurological or muscular pathology. All fibroblast cultures had undergone less than ten passages when received, and were utilized in general within two or three additional passages. Fibroblasts were cultured in DMEM supplemented with 20% FBS. For the first-DGGE analysis, internal homo-and heteroduplex formation within the PCR products from the individual fibroblast samples was obtained by a heat denaturation/cooling protocol previously detailed (Y. Michikawa, G. Hofhaus, L. S. Lerman, G. Attardi, Nucl. Acid Res. 25, 2455 (1997)). The type of broad-range denaturant gradient used, the running times, the gel apparatus and the basic conditions were optimized for each DLP fragment as described (Y. Michikawa, G. Hofhaus, L. S. Lerman, G. Attardi, Nucl. Acid Res. 25, 2455 (1997)). FIG. 2A (a) shows the DLP4 profiles of highly purified mtDNA from representative fibroblast cultures, including the two LS5 samples, FIG. 2A (b, c), the DLP6 profiles of untreated total cell DNA (b)or highly purified mtDNA (c)from the same fibroblast samples, and FIG. 2A (d), the DLP6 profiles of purified mtDNA from fibroblasts of the other eight LS individuals. The DLP4 and, especially, the DLP6 PCR products from old individuals (>65 y) show a tendency to exhibit, besides the homoduplex band and a band corresponding to uncrosslinked molecules (UX), one or more slower migrating bands, indicative of sequence variants; which result from heteroduplex formation in the final melting and annealing steps (Y. Michikawa, G. Hofhaus, L. S. Lerman, G. Attardi, Nucl. Acid Res. 25, 2455 (1997)). Especially significant is the fact that, in five of the nine LS sample pairs (LS1, LS4, LS6, LS7 and LS9), sequence variants of DLP6 appear only, or are more diverse (in LS6), in the sample taken at a more advanced age.

After the first-DGGE assays, the PCR-amplified DLP6 fragments from nearly all purified mtDNA samples and all DLP4 fragments exhibiting abnormal bands were further analyzed. For this purpose, these fragments were cloned, in *E. coli*, and a large number of plasmids (in general, 42 to 48) were isolated from each source, and their DNAs, subjected to PCR amplification and a second-DGGE step, after hybridization with a randomly chosen reference cloned fragment. pGEM-T Easy Vector System (Promega) was used for ligation of PCR products into a plasmid vector. The ligation mixtures were electroporated into Top 10 F' *E. coli* competent cells using the Gene Pulser apparatus (Bio-Rad). Plasmid DNAs were isolated from cultures derived from 45 colonies using the QIAprep8 Miniprep Kit (Qiagen). To produce intersample homo-and heteroduplexes, equal amounts of PCR products, obtained with Taq polymerase (Promega)from a reference clone and a sample clone, were mixed, overlaid by mineral oil and processed by the same heat denaturation/cooling protocol previously mentioned (Y. Michikawa, G. Hofhaus, L. S. Lerman, G. Attardi, Nucl. Acid Res. 25, 2455 (1997)). After homo-and heteroduplex formation, cross-linking between the psoralen clamp-carrying strand and the complementary psoralen-free strand was carried out as previously detailed (Y. Michikawa, G. Hoiaus, L. S. Lerman, G. Attardi, Nucl. Acid Res. 25, 2455 (1997)). The PCR products of the reference clones were subjected-to the same treatment, without, however, hybridization with other PCR products.

Figure 1D:
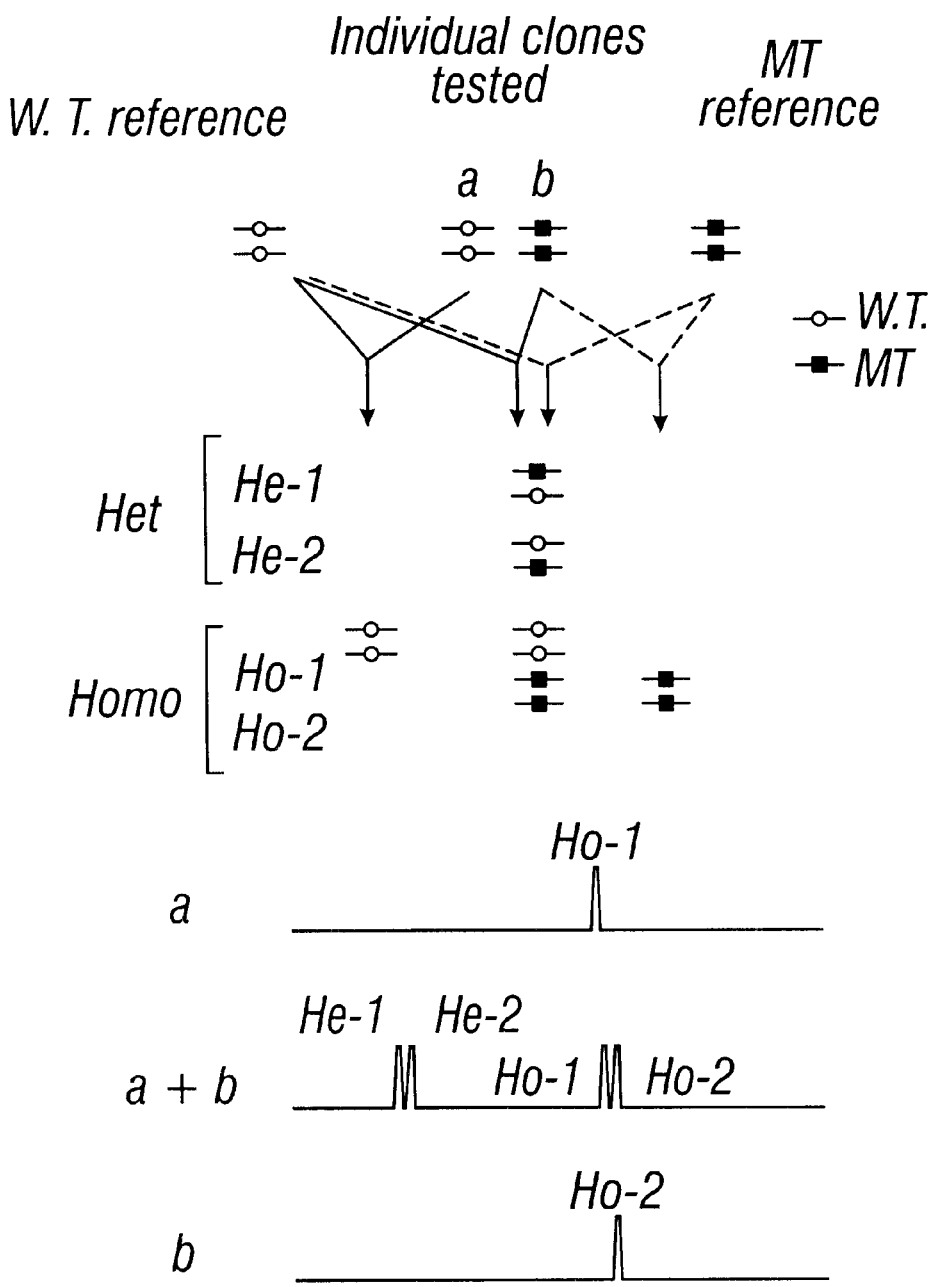

The possible patterns of homoduplexes and/or heteroduplexes expected in this hybridization step are illustrated schematically in FIG. 1D. If the randomly chosen cloned fragment to be used as a reference had a wild-type sequence, one expected that the clone tested would produce a homoduplex band, if it carried a wild-type sequence, or two heteroduplexes and two homoduplexes, both types usually migrating as single unresolved bands, if it carried a mutant sequence (FIG. 1D). If the reference clone had, on the contrary, a mutant sequence, it was expected that the clone tested would produce a homoduplex band if it carried the identical mutant sequence, or two heteroduplexes and two homoduplexes, if it carried a wild-type sequence (FIG. 1D) or a different mutant sequence. All presumptive mutant clones and several of the presumptive wild-type clones identified by the second-DGGE analysis were then sequenced, together with the reference clone(s). Sequence analysis of the plasmid DNAs was directly performed using the Dye Terminator Cycle Sequencing Kit with AmpliTaq DNA polymerage (ABI)and the 373A DNA Sequencer (ABI). Furthermore, the PCR-amplified DLP4 fragments of all individuals below 48 years in age were also directly sequenced.

FIG. 2B shows second-DGGE profiles produced by heteroduplexes between wild-type mtDNA and representative sets of cloned DLP6 fragments from 25 y (a), 100(2)y (b)and 100(3)y (c), and of cloned DLP4 fragments from 78 y (d). These profiles illustrate the main patterns of heteroplasmic point mutations detected in the samples.

Table 1 (FIG. 5) summarizes the sequence data obtained for the cloned DLP6 and DLP4 fragments analyzed in this work. Also shown in this Table are the results of two experiments aimed at estimating the background mtDNA sequence variation associated with the PCR and cloning steps. A cloned wild-type DLP6 mtDNA fragment from a 25 year-old individual and a cloned wild-type DLP4 mtDNA fragment from a 78 year-old individual were PCR reamplified, and the PCR products, recloned, and 48 cloned fragments thus isolated were then subjected to a second DGGE screening. A background level of heteroplasmy of 0 and 2% was found in the two experiments. Three main types of mutations were revealed by the sequence analysis: 1) specific point mutations, present in general in a high proportion of mtDNA molecules; 2) length and sequence variations of the HT D310 and of a (CA)n repeat; and 3) random point mutations. The age distribution and frequency of the mutations are summarized in the bar graph of FIG. 3.

Figure 3:
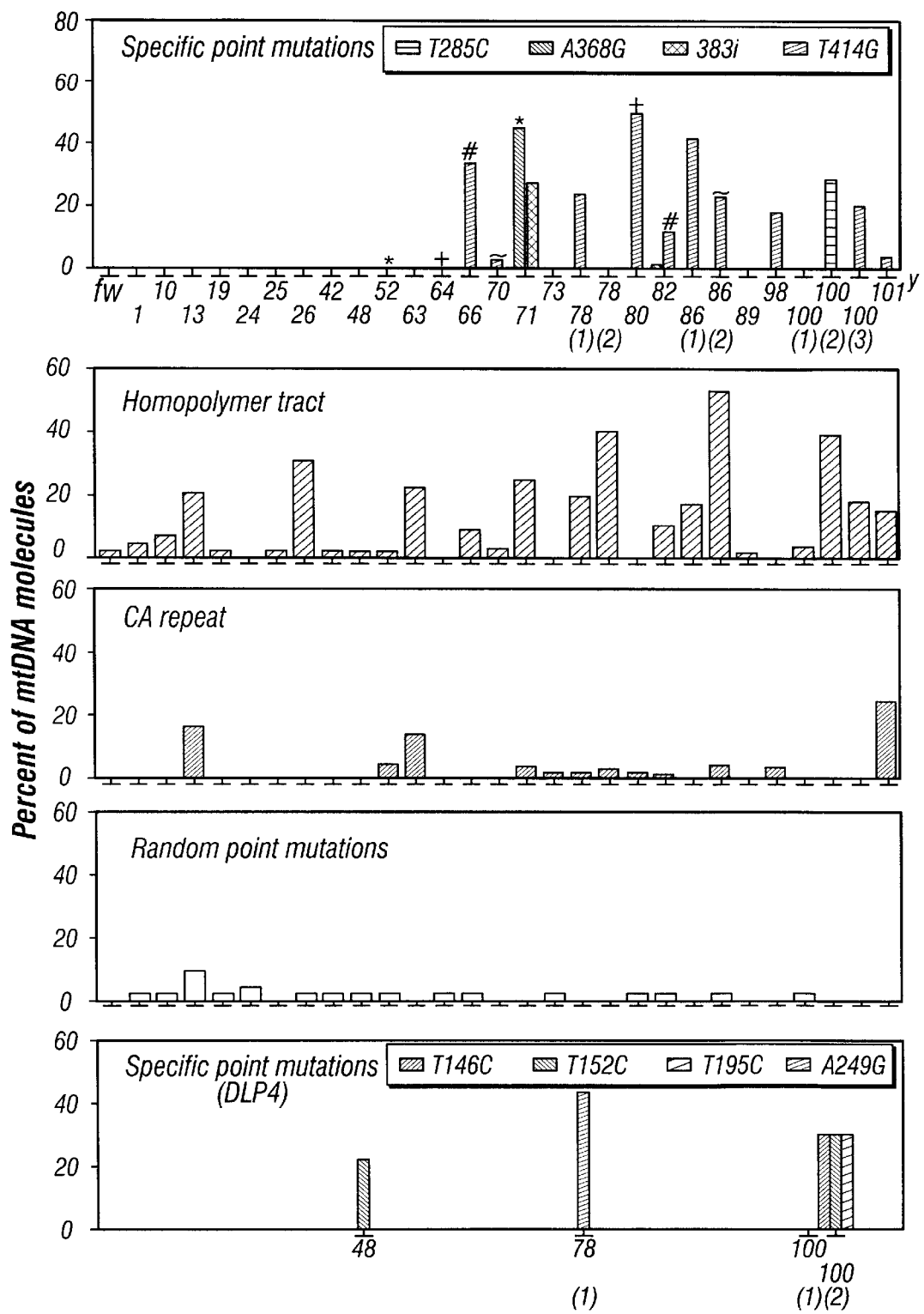
FIG. 3 is a diagram summarizing the age distribution and frequency of the various type of mutations detected in the present work. The upper four panels show the DLP6 mutations, the lowest panel shows DLP4 mutations. The dashes below each abscissae axis indicate the individuals analyzed, with the age in years (fw=20 week-fetal). In the uppermost panel, the two samples of each LS pair are indicated by a distinct symbol (*, +, #, ~)
Figure 4A:
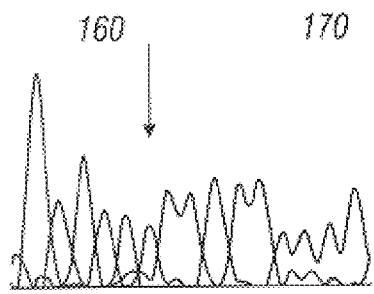
FIG. 4 shows the detection of T414G (A414C) mutation by DNA sequencing and allele-specific termination of primer extension. Sequences of DLP6 fragments amplified from highly purified fibroblast mtDNA of LS7-70 y and LS7-86(2) y, estimated to contain respectively (A) 3% and (B) 23% mutation by the DGGE-cloning-sequencing method. Primer extension data of a representative set of DLP6 fragments are shown in (C), and comparison of frequencies of mutation determined by the primer extension and the DGGE-cloning-sequencing methods are shown in (D). (A) shows the reverse complement of nucleotides 405–420 of SEQ ID NO: 1 (SEQ ID NO: 2. (B) shows the reverse complement of nucleotides 405–420 of SEQ ID NO: 1 including the T414G mutation (SEQ ID NO: 3).
Figure 4B:
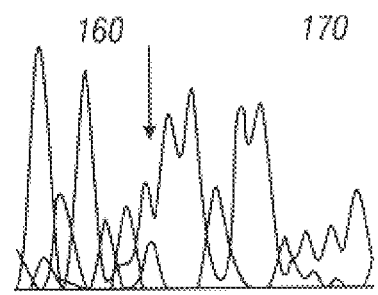
Figure 4C:
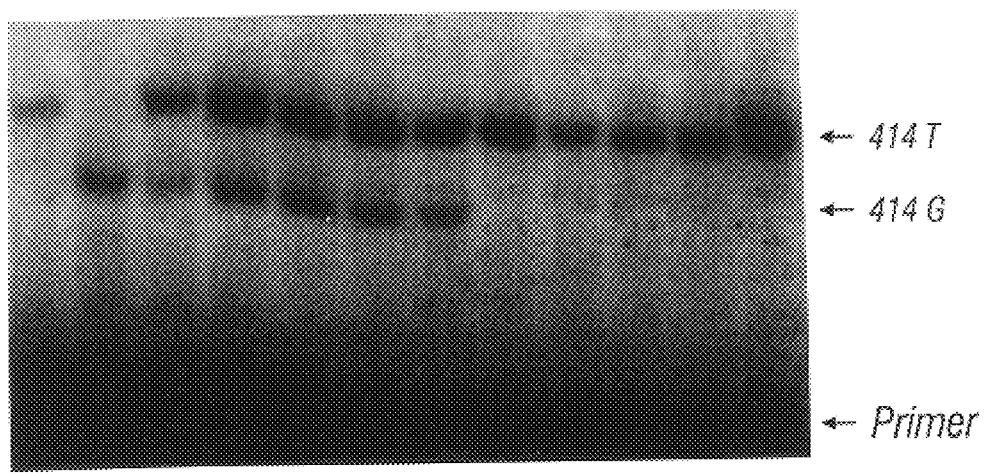
Figure 5F:
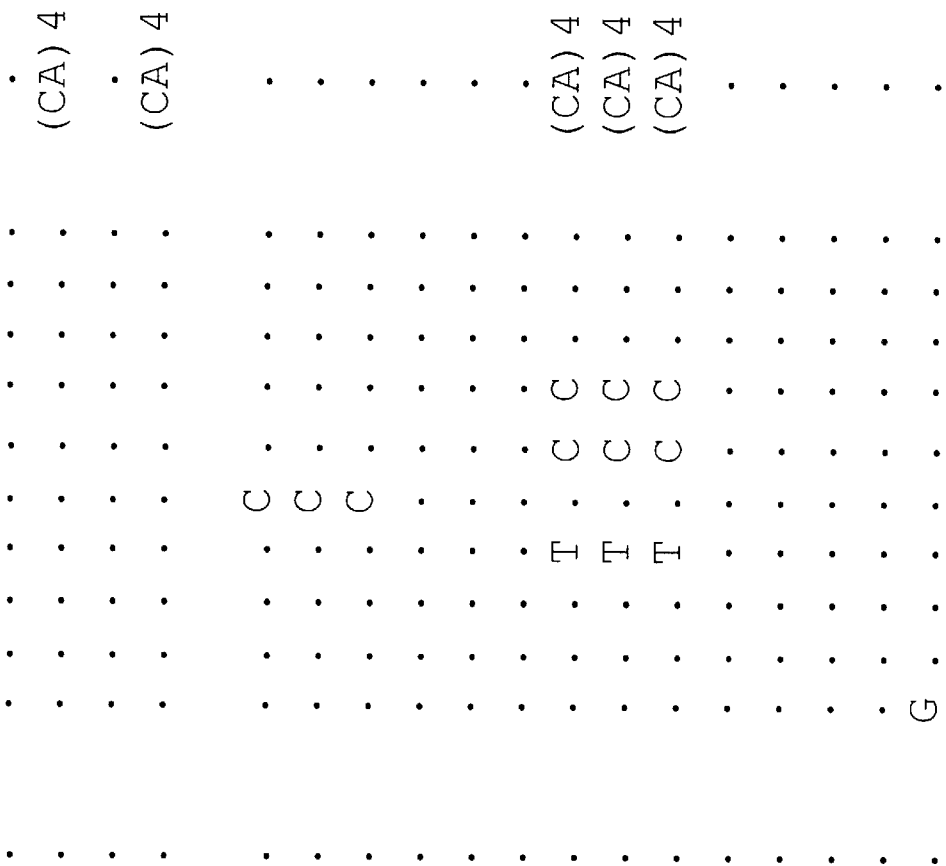
FIG. 5 shows Table 1.
Figure 5J:
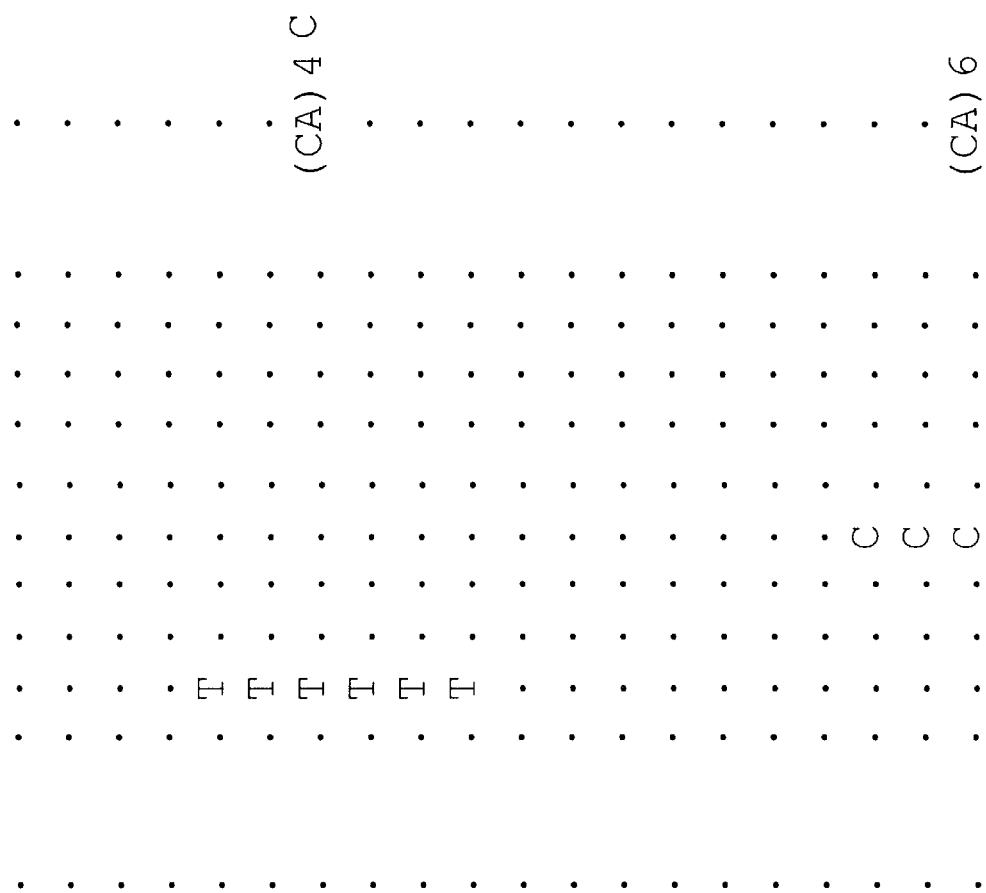
Figure 5N:
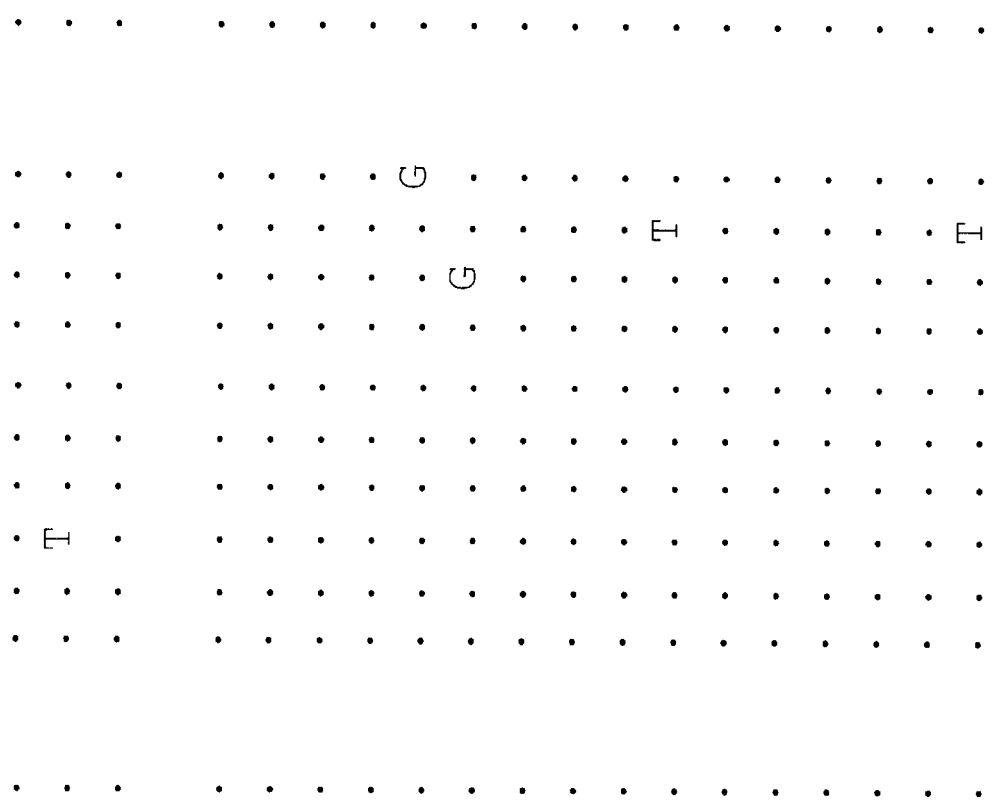
Figure 5P:
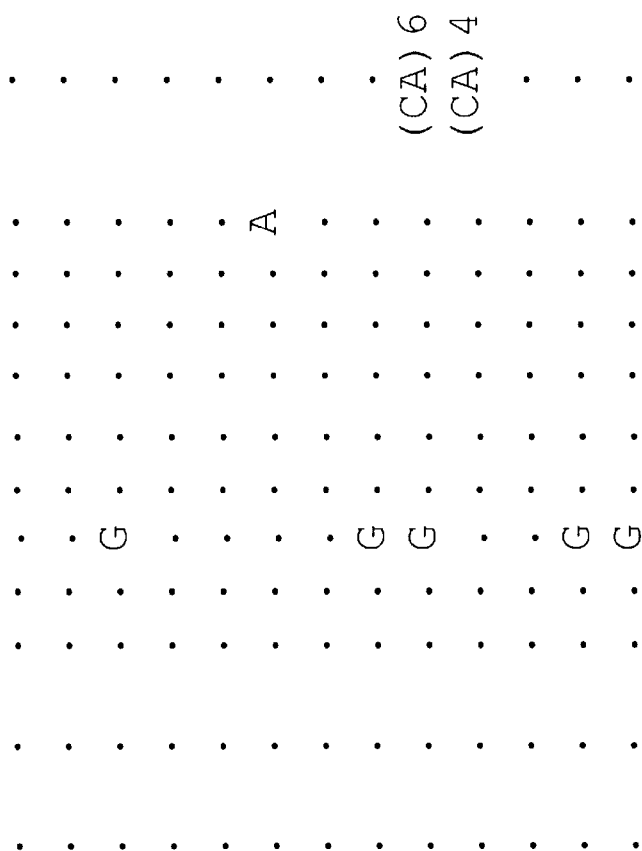
Figure 5Q:
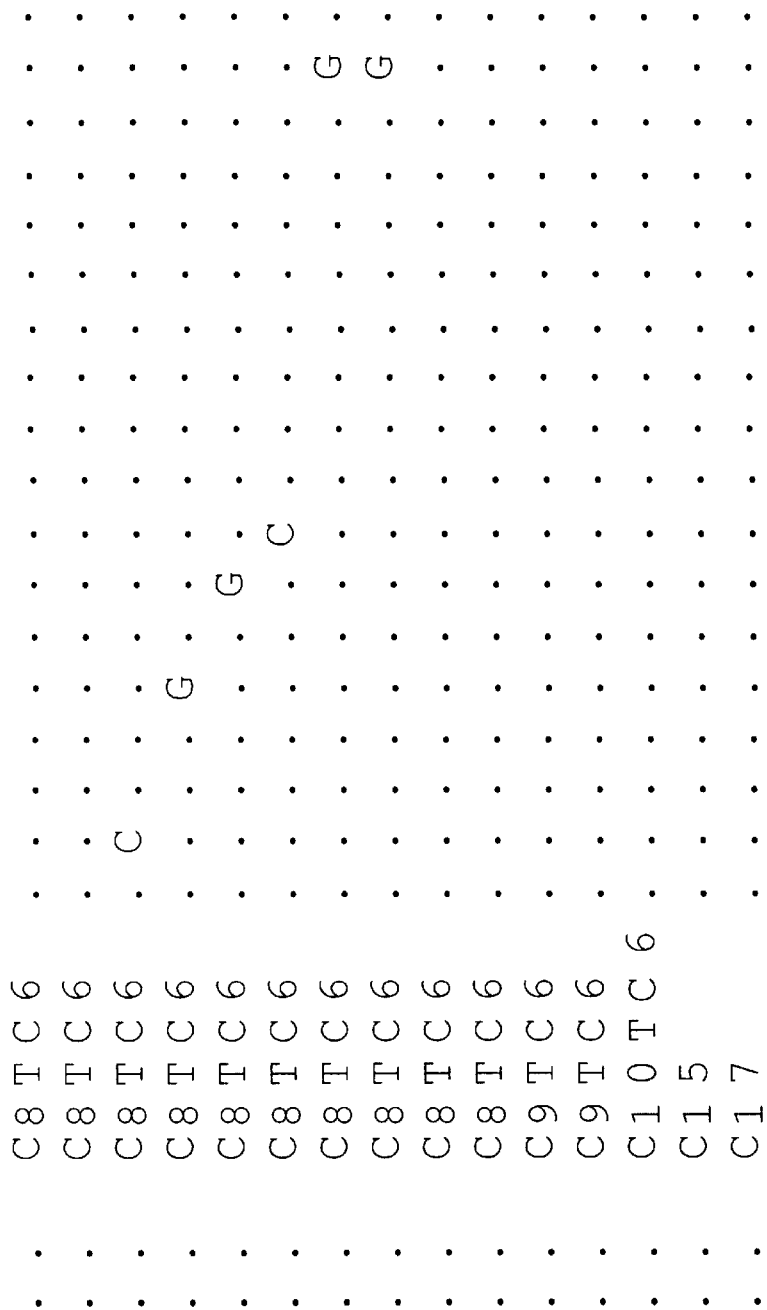

The most significant result of the sequence analygig was the finding of an aging-related accumulation of high copy specific point mutations, almost always base substitutions, in the DLP6 region. In fact, when the DLP6 plasmid clones from 10 of the 14 individuals older than 65 years were analyzed, 151 of a total of 507 carried a specific point mutation outside HT D310. The proportion of mutant clones deriving from each individual ranged in general between 21 and 50%. In contrast, no such mutation was found in DLP6 in a total of 581 plasmid clones from 13 younger individuals (FIG. 3 and FIG. 5 (Table 1)). The high frequency of each of the aging-related specific point mutations detected in the present work in human fibroblast mtDNA is in striking contrast with the generally low frequency (<1–2%)of aging-related large mtDNA deletions previously observed in the human brain and other organs. Another striking observation was the occurrence of some mutations in more than one individual. The most dramatic example was the finding of a T414G transversion in DLP6 clones derived from fibroblasts of eight genetically unrelated individuals older than 65 y (FIG. 3 and FIG. 5). It has also to be noted that no T414G transversion was found in the plasmid control.

Strong support for the age-dependency of the accumulation of point mutations in DLP6 was provided by the analysis of samples taken twice from the same individuals at a distance of time (15 to 19 years). In three such studies, the mutation was absent (LS1, LS4) or present at a marginal level (LS7)in the earlier sample, but was abundant (with a frequency of 23 to 50%) in the later sample. In another study (LS6), the T414G transversion, was found in a significant proportion of mtDNA in both the earlier and later samples, although considerably decreased in the latter. A repeat of the cloning and sequencing of the DLP6 fragments of the two LS6 samples gave results that, when combined with the previous ones, yielded a coefficient of variation for the frequency of the specific point mutations of –20%, supporting the reproducibility of the estirnates.

Two other LS studies (LS3 and LS8) did not reveal any specific mutation in either the earlier or the later sample. It is interesting that the base substitutions T414G, T285C and A368G and the T insertion after position 383, have not been reported before in human mtDNA (Kogelnik et al., Nucleic Acids Res. 26, 112, 1998).

Although more limited, the analysis of the DLP4 clones revealed the same pattern found for DLP6. Thus, a T152C transition occurred in two individuals, i.e., in 23% and 31%, respectively, of the DLP4 clones from 48 y and 100(2)y. The latter individual also exhibited, in the same 31% of its DLP4 clones, a T146C transition and a T195C transition, while 48 y exhibited in all its clones the T195C transition, which was presumably in this case an inherited polymorphism. It is interesting that the T to C transitions at positions 146, 152, and 195 have been previously described as polymorphisms (Kogelnik et al., Nucleic Acids Res. 26, 112, 1998). By contrast, the A249G transition, found in 45% of the DLP4 clones from 78 y, has not been described as a polymorphism (Kogelnik et al., Nucleic Acids Res. 26, 112, 1998). None of the high frequency base substitutions detected in the DLP4 fragments from the individuals 48 years old analyzed here was present in the DLP4 fragments of nine individuals younger than 48 years, as judged from the first-DGGE patterns and from the results of direct DNA sequencing of the PCR-amplified DLP4 fragments.

The age distribution and the results of the longitudinal studies strongly support the base substitutions identified herein are not inherited. A role of nuclear mtDNA pseudogenes in this phenomenon is excluded by several lines of strong evidence, in particular 1) the failure to obtain any PCR products with primers specific for the DLP6 and DLP4 mtDNA segments from total cell DNA of mtDNA-less p0206 cells, digested with BglII, DraIII, RNase A and ExoIII; 2) the identity of the DLP6 first-DGGE patterns obtained from total cell DNA and from purified mtDNA of individual fibroblast samples exhibiting such specific base substitutions (FIGS. 2Ab and 2Ac); 3) the absence of any of the specific base substitutions in the DLP6 and DLP4 mtDNA fragments from individuals younger than 48 years; and 4)the results of three longitudinal studies.

The specific point mutations identified in the present work may occur during aging due to oxygen radical-induced mtDNA damage or to mtDNA polymerase errors, or to a phenomenon akin to the bacterial SOS response, recently described also in yeast (N. Bather Reuven, G. Tomer, Z. Livneh, Molecular Cell 2, 191 (1998)). Whatsoever its origin, the mutation may become amplified because of the replicative advantage of the mtDNA molecules carrying them in fibroblasts from old individuals, as shown for pathogenic point mutations (M. Yoneda, T. Miyatake, G. Attardi, Molec. Cell. Biol. 14,2699 (1994))or deletions (N. G. Larsson et al., Pediatr. Res. 28, 131 (1990)). Subsequently, the cells with amplified mtDNA mutation would tend to take over the whole population as a result of clonal selection, due to the growth advantage that the mtDNA mutation or a secondary nuclear mutation confers upon the cell. The suggested occurrence of such an mtDNA replacement phenomenon has a striking similarity to that described for the homoplasmic or nearhomoplasmic somatic mutations in human colorectal tumors (K. Polyak et al., Nature Genetics 20, 291 (1998)), and the same mechanism may conceivably underlie both occurrences.

Figure 2C:
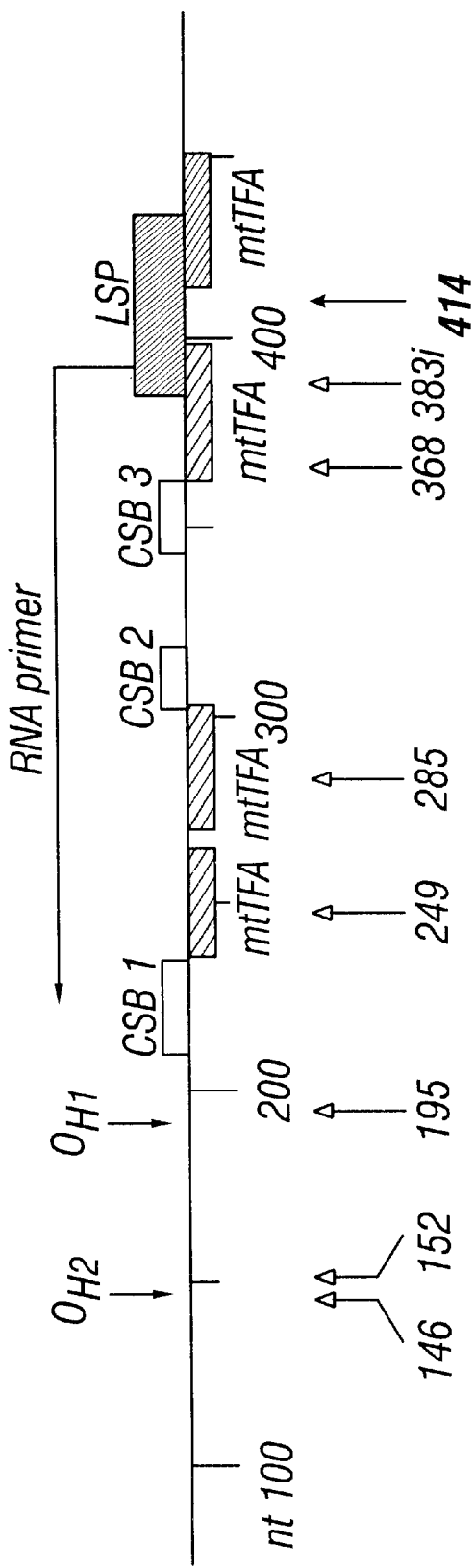
FIG. 2(A) shows ethidium bromide stained gels illustrating the first-DGGE analysis of the PCR products of the DLP4(a) and DLP6 (b–d) segments of the mtDNA main control region from total cell DNA (b) and highly purified mtDNA (a,c,d) of fibroblasts from differently aged individuals and of zhoO 206 cells. The first lanes show an uncrosslinked sample from 10 γ (a, b, and c) and from LS1-52 y (d). UX: uncrosslinked molecules. (3) Shows second-DGGE profiles of heteroduplexes between a wild-type cloned fragment and representative sets of DLP6 cloned fragments from highly purified fibroblast mtDNA of 25 y (a), 100(2) y (b) and 100(3) y (c) and of DLP4 cloned fragments from 78 y (d). The first lane in each panel shows an uncrosslinked sample from the wild-type reference clone. In panel c of 100(3) y, clones selected as representative of the different types of mtDNA sequence were analyzed in the same gel. In this panel, the random mutations, the number of C residues upstream (u) of T at position 310 in the D310 homopolymeric tract (HT'u. C's) and the nucleotide at position 414 in the various clones are indicated. (C) Shows Scheme 1 of a portion of the mtDNA main control region showing the positions of the specific mutations identified in the present work. The positions of binding of the mtTFA transcription factor (the densely hatched rectangle indicates a position of high affinity binding) and the site of the promoter for L-strand transcription (LSP) are shown. The homopolymer tract D310 is located within CSB 2. OH1, primary initiation site and OH2, secondary initiation site of mtDNA H-strand synthesis. 383i: T insertion after position 383.

As concerns the possible functional effects of the specific point mutations detected in the present work, it is interesting that the T414G transversion occurs in the middle of the promoter for mtDNA H-strand synthesis primer synthesis and L-strand transcription (LSP), at a position immediately adjacent to a segment with high affinity for the mtTFA transcription factor (S. C. Ghivizzani et al., Molec. Cell. Biol. 14,7717 (1994))(FIG. 2C). Also the other seven specific mutations observed in old individuals occur at positions critical for mtDNA replication, in particular, either in the coding sequence of the RNA primer for H-strand synthesis, within mtTFA binding segments (S. C. Ghivizzani et al., Molec. Cell. Biol. 14,7717 (1994)), or very close to the OH1 primary site, or to the OH2 secondary site of DNA synthesis initiation (S. C. Ghivizzani et al., Molec. Cell. Biol. 14,7717 (1994))(FIG. 2C). It is important to mention that the specific mutations detected here occur in DNA sequences which have been shown to either undergo unwinding and bending due to mtTFA binding at the same or an adjacent position (S. C. Ghivizzani et al., Molec. Cell. Biol. 14,7717 (1994); R. P. Fisher, T. Lisowsky, M. A. Parisi, D. A. Clayton, J. Biol. Chem. 267, 3358 (1992)), or to form persistent RNA-DNA hybrids, giving rise to an R loop with a tRNA-like cloverleaf structure, at the origin(s)of H-strand synthesis (D. Y. Lee, D. A. Clayton, Genes & Development 11, 582 (1997); D. Y. Lee, D. A. Clayton, J. Biol. Chem. 273, 30614-(1998)). The conformational changes mentioned above are expected to expose single-stranded DNA stretches, which may be more susceptible to oxygen radical damage. The positions of the specific point mutations detected in the present work and their abundance strongly point to a functional role, with implications for a possible mitochondrial involvement in aging-related degenerative diseases.

A detailed analysis of Table 1 (FIG. 5) shows that the length and sequence variation of HT D310 detected here was more extensive than previously reported (D. R. Marchington, G. M. Hartshorne, D. Barlow, J. Poulton, Am. J. Hum. Genet. 60, 408 (1997)). The number of different isoforms in each individual varied between 1 and 5, and the proportion of mtDNA molecules with variant tract length ranged between 0 and 54%, with a slight tendency of the length variation to increase with age (FIG. 3 and FIG. 5). However, neither the D310 nor the (CA), length variation was restricted to old individuals, thus providing a striking contrast to the behavior of the specific point mutations (FIG. 3). Similarly, DLP6 clone sets carrying random base substitutions and rare single base deletions with an overall frequency (4–11%)higher than the background level (~2%)were isolated from mtDNA samples of both young and old individuals, though with a tendency to be more common in the latter (FIG. 3 and FIG. 5). These mutations did not appear to be preferentially located at or near functionally critical positions. Among the random heteroplasmic base substitutions, transitions were much more frequent than transversions (78% versus 22%), in agreement with the mutational bias previously reported for polymorphisms (M. Hasegawa, S. Horai, J. Mol. Evol. 32, 37 (1991); M. Stoneking et al., Am. J. Hum. Genet. 48,370 (1991), T. J. Pargons e al., Nature Genet. 15,363 (1997); B. D. Greenberg, J. E. Newbold, A. Sugino, Gene 21,33 (1983)).

```

What is claimed is:

1. An isolated polynucleotide comprising SEQ ID NO: 1 with the exception that said isolated polynucleotide has a G at position 414 of SEQ ID NO: 1.

2. The isolated polynucleotide of claim 1, operably linked to a reporter gene.

3. The isolated polynucleotide of claim 2, wherein the reporter gene is selected from the group consisting of galactosidase, luciferase, and alkaline phosphatase.

4. A vector containing the isolated polynucleotide of claim 1.

5. The vector of claim 4, wherein the vector is an expression vector.

6. The vector of claim 5, wherein the vector is a viral vector.

7. The vector of claim 5, wherein the vector is a plasmid.

8. A host cell containing the vector of claim 4.

9. A culture comprising the host cell of claim 8, wherein the conditions present in said culture allow expression of the isolated polynucleotide.

10. A kit useful for the detection of an age-related mutation of mitochondrial DNA comprising carrier means containing therein one or more containers wherein a first container contains a nucleic acid probe that specifically hybridizes to a nucleic acid sequence as set forth in SEQ ID NO: 1 with the exception that said sequence has a G at position 414 of SEQ ID NO: 1.

11. The kit of claim 10, wherein the probe is detectably labeled.

12. The kit of claim 11, wherein the label is selected from the group consisting of radioisotope, a bioluminescent compound, a chemiluminescent compound, a fluorescent compound, a metal chelate, and an enzyme.

* * * * *

                            SEQUENCE LISTING

<160> NUMBER OF SEQ ID NOS: 3

<210> SEQ ID NO 1
   <211> LENGTH: 660
   <212> TYPE: DNA
   <213> ORGANISM: Homo sapiens

<400> SEQUENCE: 1
gatcacaggt ctatcaccct attaaccact cacgggagct ctccatgcat ttggtatttt      60
cgtctggggg gtatgcacgc gatagcattg cgagacgctg gagccggagc accctatgtc     120
gcagtatctg tctttgattc ctgcctcatc ctattattta tcgcacctac gttcaatatt     180
acaggcgaac atacttacta aagtgtgtta attaattaat gcttgtagga cataataata     240
acaattgaat gtctgcacag ccactttcca cacagacatc ataacaaaaa atttccacca     300 aacccccct cccccgcttc tggccacagc acttaaacac atctctgcca aacccaaaa     360 acaaagaacc ctaacaccag cctaaccaga tttcaaattt tatctttttgg cggtatgcac     420 ttttaacagt cacccccaa ctaacacatt attttccct cccactccca tactactaat     480
ctcatcaata caaccccgc ccatcctacc cagcacacac acaccgctgc taaccccata     540
ccccgaacca accaaacccc aaagacaccc cccacagttt atgtagctta cctcctcaaa     600
gcaatacact gaaaatgttt agacgggctc acatcacccc ataaacaaat aggtttggtc     660

<210> SEQ ID NO 2
   <211> LENGTH: 17
   <212> TYPE: DNA
   <213> ORGANISM: Artificial sequence
   <220> FEATURE:
   <223> OTHER INFORMATION: Primer for PCR

<400> SEQUENCE: 2
gtgcataccg ccaaaag                                                     17

<210> SEQ ID NO 3
   <211> LENGTH: 17
   <212> TYPE: DNA
   <213> ORGANISM: Artificial sequence
   <220> FEATURE:
   <223> OTHER INFORMATION: Primer for PCR

<400> SEQUENCE: 3
gtgcatcccg ccaaaag                                                     17
```